United States Patent
Kreutz

(10) Patent No.: US 9,320,785 B2
(45) Date of Patent: Apr. 26, 2016

(54) AUTOLOGOUS CANCER CELL VACCINE

(71) Applicant: Fernando Thome Kreutz, Porto Alegre (BR)

(72) Inventor: Fernando Thome Kreutz, Porto Alegre (BR)

(*) Notice: Subject to any disclaimer, the term of this patent is extended or adjusted under 35 U.S.C. 154(b) by 308 days.

(21) Appl. No.: 13/744,755

(22) Filed: Jan. 18, 2013

(65) Prior Publication Data

US 2013/0189310 A1     Jul. 25, 2013

Related U.S. Application Data

(60) Provisional application No. 61/589,123, filed on Jan. 20, 2012.

(51) Int. Cl.
    *A61K 39/00*          (2006.01)

(52) U.S. Cl.
    CPC ..... *A61K 39/0011* (2013.01); *A61K 2039/5152* (2013.01); *A61K 2039/5158* (2013.01); *A61K 2039/55* (2013.01); *A61K 2039/585* (2013.01)

(58) Field of Classification Search
None
See application file for complete search history.

(56) References Cited

U.S. PATENT DOCUMENTS

| | | | | |
|---|---|---|---|---|
| 5,494,673 | A | * | 2/1996 | Andrianov et al. ........ 424/280.1 |
| 5,994,082 | A | * | 11/1999 | Mach ..................... G01N 33/68 435/7.1 |
| 2002/0018766 | A1 | | 2/2002 | Roberts et al. |
| 2008/0050395 | A1 | | 2/2008 | Gerber |
| 2010/0092499 | A1 | | 4/2010 | Moviglia et al. |
| 2011/0165190 | A1 | * | 7/2011 | Watkins et al. ............ 424/208.1 |

FOREIGN PATENT DOCUMENTS

| | | | |
|---|---|---|---|
| WO | WO89/10755 | * | 11/1989 |
| WO | WO-95/13092 A1 | | 5/1995 |
| WO | WO-95/16775 A1 | | 6/1995 |
| WO | WO99/45954 | * | 11/1999 |
| WO | WO-01/77301 A1 | | 10/2001 |
| WO | WO2009/114085 | * | 11/2009 |

OTHER PUBLICATIONS

Dissanayake et al (Cancer Research, 2004, vol. 64, pp. 1867-1874).*
Alexander et al (Journal of Immunology, 1989, vol. 142, pp. 4070-4078).*
Trefzer et al (Molecular Biotechnology, 2003, vol. 25, pp. 63-69).*
Panina-Bordignon et al (European Journal of Immunology, 1989, vol. 19, pp. 2237-2242).*
Trefzer et al (Methods in Molecular Medicine, 2000, vol. 35, pp. 469-475).*
Freshney (The Culture of Animal Cells, 1994, p. 254).*
"International Application Serial No. PCT/BR2013/000047, International Search Report mailed Jun. 3, 2013", 4 pgs.
"International Application Serial No. PCT/BR2013/000047, Written Opinion mailed Jun. 3, 2013", 16 pgs.
Gong, J., et al., "Activation of antitumor cytotoxic T lymphocytes by fusions of human dendritic cells and breast carcinoma cells", *Proc. Natl. Acad. Sci. USA*, 97(6), (2000), 2715-2718.
Trefzer, U., et al., "Hybrid Cell Vaccination for Cancer Immune Therapy: First Clinical Trial with Metastatic Melanoma", *Int. J. Cancer*, 86(5), (2000), 618-626.
Berger, Milton, et al., "Phase I study with an autologous tumor cell vaccine for locally advanced or metastatic prostate cancer", J Pharm Pharmaceut Sci (www. cspsCanada.org) 10 (2): 144-152, 2007, (Jun. 14, 2007), 144-152.
Pisapia, Laura, et al., "Contrasting effects of IFN® on MHC class II expression in professional vs. nonprofessional APCs: Role of CIITA type IV promoter", Results in Immunology 2 (2012) 174-183, (Sep. 19, 2012), 174-183.

* cited by examiner

*Primary Examiner* — Karen Canella
(74) *Attorney, Agent, or Firm* — Schwegman, Lundberg & Woessner, P.A.

(57) ABSTRACT

An autologous cancer cell vaccine comprises cancer cells that express both MHCI and MHCII on their cell surface. The MHCI presents a cancer antigen and the MHCII presents a non-self antigen.

56 Claims, 14 Drawing Sheets

A

B

C

AUTOLOGOUS CANCER CELL VACCINE

CROSS-REFERENCE TO RELATED APPLICATIONS

This application claims the benefit of priority under 35 U.S.C. §119(e) to U.S. Provisional Patent Application No. 61/589,123, filed on Jan. 20, 2012, titled "AUTOLOGOUS CANCER CELL VACCINE," which is incorporated herein by reference in its entirety.

FIELD OF THE INVENTION

The present invention relates to the treatment of cancer. More specifically, the present invention is, in aspects, concerned with isolated and altered immunogenic cancer cells, immunogenic compositions and vaccines comprising the immunogenic cancer cells, methods for the treatment of cancer, as well as methods for making the immunogenic cancer cells, immunogenic compositions, and vaccines.

BACKGROUND OF THE INVENTION

Major histocompatibility complex (MHC) is a cell surface molecule encoded by a large gene family in all vertebrates. The MHC gene family is divided into three classes: class I; class II; and class III.

MHC class I molecules are found on every nucleated cell of the body. Their function is to present fragments of cytosolic proteins from within the cell to cytotoxic T cells. Cells presenting "self" peptides will be ignored, whereas cells presenting non-self peptides will be recognized and killed by the cytotoxic T cells.

MHC class II molecules are found only on antigen presenting cells (APCs), including macrophages, dendritic cells, and B cells. MHC class II molecules present fragments of extracellular proteins to helper T cells. Cells presenting "self" peptides will be ignored, whereas cells presenting non-self peptides will be recognized by the helper T cells, which help to trigger an appropriate immune response, mainly via production of various cytokines, that may include localized inflammation and swelling due to recruitment of phagocytes or an antibody-mediated immune response due to activation of B cells.

It is known from, for example, International Patent Application Publication No. WO 1995/13092, International Patent Application Publication No. WO 2001/77301 and Berger et al. (J. Pharm. Pharmaceut. Sci., 10(2):144-152, 2007) that interferon (IFN) can be used to increase expression of MHC class I on tumour cells, so that the cells may be used in a cancer vaccine. However, MHCII expression by tumour cells following treatment with IFN is highly variable, with some cells being responsive to IFN treatment and some being unresponsive to IFN treatment. Moreover, any tumour cells that express MHCII could only present self or cancer antigens in the context of MHCI and MHCII. Cancer antigens are not consistently immunogenic, as many are recognized as self antigens. This is particularly true as the cancer develops and becomes more aggressive. The lack of a highly immunogenic antigen being presented in the context of MHCII means that T helper cells will not be activated and a strong and robust immune response cannot be consistently produced by the cancer vaccines of the prior art.

Accordingly, there is a need for alternative therapies to overcome or mitigate at least some of the deficiencies of the prior art.

SUMMARY OF THE INVENTION

The present invention relates, in aspects, to isolated immunogenic cancer cells, immunogenic compositions and cancer vaccines using the immunogenic cancer cells, methods of making such immunogenic cancer cells, immunogenic compositions, and cancer vaccines, and methods for the treatment of cancer. The compositions and methods of the invention involve the use of isolated cancer cells that have been modified to express MHCII on their surface. Once the cancer cells have been modified to express MHCII, they are rendered immunogenic by incubating the MHCII-expressing cells with a non-self antigen. Upon injection into the subject from whom they were isolated, cancer cells modified in this way will present a cancer antigen in the context of MHCI to $CD8^+$ cytotoxic T cells and will present the non-self antigen to $CD4^+$ helper T cells in the context of MHCII. Thus, the modified cancer cells are bifunctional, being capable of activating both helper T cells and cytotoxic T cells, leading to cytokine production and a surprisingly robust and cancer-specific immune response.

Immunogenic cancer cells produced in this way may be incorporated into immunogenic compositions and vaccines. Such compositions and vaccines are useful in methods of treating cancer in an autologous subject.

In accordance with an aspect, there is provided a method for making isolated immunogenic cancer cells, the method comprising:
  inducing expression of MHCII on cancer cells isolated from a subject;
  incubating the cancer cells with a non-self antigen so that the non-self antigen will be bound to expressed MHCII; and
  killing the cancer cells.

In an aspect, the method further comprises identifying MHCII-positive cells after MHCII induction. In another aspect, the method further comprises separating the MHCII-positive cancer cells from MHCII-negative cancer cells to obtain a purified composition containing the MHCII-positive cells.

In another aspect, the method further comprises isolating the cancer cells from a subject. In an aspect, said cells are isolated during a biopsy procedure or during surgical removal of a tumour.

In another aspect, the method further comprises cryo-preserving the cancer cells.

In an aspect, the cells are killed by lethal irradiation, freezing and thawing in the absence of a cryo-preservation agent, or treatment with a cytotoxic compound, such as by lethal irradiation.

In another aspect, the MHCII is induced on the cancer cells using an MHCII-inducing agent. In an aspect, the MHCII-inducing agent is a cytokine, such as IFN-α, IFN-β, IFN-γ, IL-4, IL-13, IL-23, TNF-α, or a combination thereof, such as IFN-γ. In another aspect, the MHCII-inducing agent is an MHCII expression construct or an MHCII-expressing cell that will fuse with the cancer cells.

In another aspect, the non-self antigen is a non-human antigen.

In another aspect, the non-self antigen is selected from thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH), and a combination thereof, such as ovalbumin or KLH, or such as BSA.

In another aspect, said non-self antigen is not a bovine antigen, such as BSA.

In another aspect, said inducing step is in a medium free of BSA.

In accordance with another aspect, there is provided isolated immunogenic cancer cells that express both MHCI and MHCII on their cell surface, wherein a cancer antigen is bound to said MHCI and a non-self antigen is bound to said MHCII.

In an aspect, the non-self antigen is a non-human antigen.

In another aspect, said non-self antigen is selected from thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH), and a combination thereof, such as non-self antigen is ovalbumin or KLH, or such as BSA.

In another aspect, said non-self antigen is not a bovine antigen, such as BSA.

In accordance with another aspect, there is provided an immunogenic composition comprising isolated immunogenic cancer cells that express both MHCI and MHCII on their cell surface, wherein a cancer antigen is bound to said MHCI and a non-self antigen is bound to said MHCII.

In an aspect, the composition further comprises at least one excipient, carrier, buffer, stabilizer, or a combination thereof.

In another aspect, the non-self antigen is a non-human antigen.

In another aspect, said non-self antigen is selected from thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH), and a combination thereof, such as ovalbumin or KLH or such as BSA.

In another aspect, said non-self antigen is not a bovine antigen, such as BSA.

In another aspect, the composition comprises from about 5% to about 100% MHCII-positive cancer cells, based on the total number of cells in the composition, such as at least about 50% MHCII-positive cancer cells, at least about 90% MHCII-positive cancer cells, or at least about 99% MHCII-positive cancer cells.

In accordance with another aspect, there is provided an autologous cancer vaccine comprising isolated immunogenic cancer cells that express both MHCI and MHCII on their cell surface, wherein a cancer antigen is bound to said MHCI and a non-self antigen is bound to said MHCII.

In an aspect, the vaccine further comprises at least one adjuvant, such as monophosphoryl Lipid A/synthetic trehalose dicorynomycolate (MPL-TDM), AS021/AS02, nonionic block co-polymer adjuvants, CRL 1005, aluminum phosphates, AIPO4), R-848, imiquimod, PAM3CYS, poly (I:C), loxoribine, bacille Calmette-Guerin (BCG), Corynebacterium parvum, CpG oligodeoxynucleotides (ODN), cholera toxin derived antigens, CTA 1-DD, lipopolysaccharide adjuvants, complete Freund's adjuvant, incomplete Freund's adjuvant, saponin, mineral gels, aluminum hydroxide, surface active substances, lysolecithin, pluronic polyols, polyanions, peptides, oil or hydrocarbon emulsions in water, MF59, Montanide ISA 720, keyhole limpet hemocyanins (KLH), dinitrophenol, and combinations thereof, such as BCG.

In another aspect, the vaccine further comprises at least one excipient, carrier, buffer, stabilizer, or a combination thereof.

In an aspect, the non-self antigen is a non-human antigen.

In another aspect, said non-self antigen is selected from thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH), and a combination thereof, such as ovalbumin or KLH, or such as BSA.

In another aspect, said non-self antigen is not a bovine antigen, such as BSA.

In another aspect, the vaccine comprises from about 5% to about 100% MHCII-positive cancer cells, based on the total number of cells in the vaccine, such as at least about 50% MHCII-positive cancer cells, at least about 90% MHCII-positive cancer cells, or at least about 99% MHCII-positive cancer cells.

In another aspect, the vaccine is provided in divided doses for multiple inoculations, such as seven divided doses.

In an aspect, each dose comprises from about $1\times10^4$ to about $1\times10^9$ cancer cells, such as about $1\times10^7$ cancer cells.

In accordance with another aspect, there is provided a method for treating cancer in a subject, the method comprising administering isolated immunogenic cancer cells to the subject, wherein the cells are autologous to the subject and express both MHCI and MHCII on their cell surface, and wherein a cancer antigen is bound to said MHCI and a non-self antigen is bound to said MHCII.

In an aspect, the cells are formulated as an immunogenic composition. In another aspect, the cells are formulated as a cancer vaccine.

In another aspect, the non-self antigen is a non-human antigen.

In another aspect, said non-self antigen is selected from thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH), and a combination thereof, such as ovalbumin or KLH, or such as BSA.

In an aspect, the non-self antigen is not a bovine antigen, such as BSA.

In another aspect, from about 5% to about 100% of the cancer cells administered are MHCII-positive cancer cells, based on the total number of cells administered, such as at least about 50% of the cancer cells administered are MHCII-positive cancer cells, at least about 90% of the cancer cells administered are MHCII-positive cancer cells, or at least about 99% of the cancer cells administered are MHCII-positive cancer cells.

In an aspect, the cells are administered concurrently or sequentially with at least one of conventional chemotherapy, radiotherapy, hormone therapy, and biotherapy.

In another aspect, the cells are administered before or after surgical tumour resection.

In another aspect, the cells are administered in multiple doses.

In an aspect, the cells are administered weekly for a predetermined number of weeks. In another aspect, the cells are administered as an ongoing maintenance therapy.

In an aspect, the cells are administered weekly, monthly, every 3 months, every 6 months, yearly, or a combination thereof.

In another aspect, the cells are administered when a sign of cancer relapse is observed.

In accordance with another aspect, there is provided a use of isolated immunogenic cancer cells autologous to a subject for treating cancer in the subject, wherein the cells express both MHCI and MHCII on their cell surface, and wherein a cancer antigen is bound to said MHCI and a non-self antigen is bound to said MHCII.

In an aspect, the cells are formulated as an immunogenic composition or as a cancer vaccine.

In another aspect, the non-self antigen is a non-human antigen.

In another aspect, said non-self antigen is selected from thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH), and a combination thereof, such as ovalbumin or KLH, or such as BSA.

In another aspect, said non-self antigen is not a bovine antigen, such as BSA.

In another aspect, the use comprises use of from about 5% to about 100% of MHCII-positive cancer cells, based on the total number of cells, such as at least about 50% MHCII-positive cancer cells, at least about 90% MHCII-positive cancer cells, or at least about 99% MHCII-positive cancer cells.

In an aspect, the cells are for use concurrently or sequentially with at least one of conventional chemotherapy, radiotherapy, hormone therapy, and biotherapy.

In another aspect, the cells are for use before or after surgical tumour resection.

In another aspect, the cells are for use in multiple doses.

In an aspect, the cells are for use weekly for a pre-determined number of weeks or for use as an ongoing maintenance therapy.

In another aspect, the cells are for use weekly, monthly, every 3 months, every 6 months, yearly, or a combination thereof.

In another aspect, the cells are for use when a sign of cancer relapse is observed.

In accordance with another aspect, there is provided a method for determining whether a patient is a candidate for therapy with isolated immunogenic cancer cells, the method comprising:
 treating isolated cancer cells from a subject with an MHCII-inducing agent; and
 screening the cancer cells to determine the presence of expressed MHCII;
 wherein the presence of expressed MHCII on the cancer cells indicates that the patient is a candidate for the therapy.

In an aspect, the method further comprises isolating the cancer cells from a subject.

In another aspect, said cells are isolated during a biopsy procedure or during surgical removal of a tumour.

In another aspect, the MHCII-inducing agent is a cytokine, such as IFN-α, IFN-β, IFN-γ, IL-4, IL-13, IL-23, TNF-α, or a combination thereof, such as IFN-γ.

In another aspect, the MHCII-inducing agent is an MHCII expression construct or an MHCII-expressing cell that will fuse with the cancer cells.

In accordance with another aspect, there is provided a cancer vaccine for immunizing a subject with cancer, the cancer vaccine comprising isolated immunogenic cancer cells autologous to the subject, wherein the cancer cells have been modified by treatment with an MHCII-inducing agent followed by incubation with a non-self antigen to thereby present the non-self antigen in the context of MHCII on their cell surface, and wherein the cancer vaccine has been purified so as to comprise an increased concentration of MHCII-expressing cells.

In accordance with another aspect, there is provided a method for making an immunogenic extract, the method comprising:
 inducing expression of MHCII on cancer cells isolated from a subject;
 incubating the cancer cells with a non-self antigen so that the non-self antigen will be bound to expressed MHCII; and
 extracting the MHCII having bound non-self antigen from the cancer cells.

In an aspect, the immunogenic extract is a membrane fraction. In another aspect, the immunogenic extract comprises purified MHCII.

In another aspect, the method further comprises identifying MHCII-positive cells after MHCII induction.

In another aspect, the method further comprises separating the MHCII-positive cancer cells from MHCII-negative cancer cells to obtain a purified composition containing the MHCII-positive cells.

In another aspect, the method further comprises isolating the cancer cells from a subject. In an aspect, said cells are isolated during a biopsy procedure or during surgical removal of a tumour.

In another aspect, the method further comprises cryo-preserving the cancer cells.

In another aspect, the cells are killed by lethal irradiation, freezing and thawing in the absence of a cryo-preservation agent, or treatment with a cytotoxic compound, such as by lethal irradiation.

In another aspect, the MHCII is induced on the cancer cells using an MHCII-inducing agent, such as a cytokine, such as IFN-α, IFN-β, IFN-γ, IL-4, IL-13, IL-23, TNF-α, or a combination thereof, such as IFN-γ.

In another aspect, the MHCII-inducing agent is an MHCII expression construct or an MHCII-expressing cell that will fuse with the cancer cells.

In another aspect, the non-self antigen is a non-human antigen.

In an aspect, said non-self antigen is selected from thyroglobulin, β-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH), and a combination thereof, such as ovalbumin or KLH, or such as BSA.

In another aspect, said non-self antigen is not a bovine antigen, such as BSA.

In another aspect, said inducing step is in a medium free of BSA.

In accordance with another aspect, there is provided an immunogenic extract of the cells of described herein, wherein the extract comprises MHCII having bound non-self antigen from the cells.

In an aspect, the extract is a membrane fraction. In another aspect, the extract comprises purified MHCII.

In accordance with another aspect, there is provided an immunogenic composition comprising the extract described herein.

In an aspect, the composition further comprises at least one excipient, carrier, buffer, stabilizer, or a combination thereof.

In accordance with another aspect, there is provided an autologous cancer vaccine comprising the extract described herein.

In an aspect, the vaccine further comprises at least one adjuvant, such as monophosphoryl Lipid A/synthetic trehalose dicorynomycolate (MPL-TDM), AS021/AS02, nonionic block co-polymer adjuvants, CRL 1005, aluminum phosphates, AlPO4), R-848, imiquimod, PAM3CYS, poly (I:C), loxoribine, bacille Calmette-Guerin (BCG), Corynebacterium parvum, CpG oligodeoxynucleotides (ODN), cholera toxin derived antigens, CTA 1-DD, lipopolysaccharide adjuvants, complete Freund's adjuvant, incomplete Freund's adjuvant, saponin, mineral gels, aluminum hydroxide, surface active substances, lysolecithin, pluronic polyols, polyanions, peptides, oil or hydrocarbon emulsions in water, MF59, Montanide ISA 720, keyhole limpet hemocyanins (KLH), dinitrophenol, and combinations thereof, such as BCG.

In another aspect, the vaccine further comprises at least one excipient, carrier, buffer, stabilizer, or a combination thereof.

In accordance with another aspect, there is provided a method for treating cancer in a subject, the method comprising administering the extract described herein to the subject, wherein the cells are autologous to the subject.

In an aspect, the extract is formulated as an immunogenic composition. In another aspect, the extract is formulated as a cancer vaccine.

In another aspect, the extract is administered concurrently or sequentially with at least one of conventional chemotherapy, radiotherapy, hormone therapy, and biotherapy.

In another aspect, the extract is administered before or after surgical tumour resection.

In another aspect, the extract is administered in multiple doses.

In another aspect, the extract is administered weekly for a pre-determined number of weeks.

In another aspect, the extract is administered as an ongoing maintenance therapy.

In another aspect, the extract is administered weekly, monthly, every 3 months, every 6 months, yearly, or a combination thereof.

In another aspect, the extract is administered when a sign of cancer relapse is observed.

In accordance with another aspect, there is provided a use of the extract described herein for treating cancer in a subject, wherein the cells are autologous to the subject.

In an aspect, the extract is formulated as an immunogenic composition. In another aspect, the extract is formulated as a cancer vaccine.

In another aspect, the extract is for use concurrently or sequentially with at least one of conventional chemotherapy, radiotherapy, hormone therapy, and biotherapy.

In another aspect, the extract is for use before or after surgical tumour resection.

In another aspect, the extract is for use in multiple doses.

In another aspect, the extract is for use weekly for a pre-determined number of weeks.

In another aspect, the extract is for use as an ongoing maintenance therapy.

In another aspect, the extract is for use weekly, monthly, every 3 months, every 6 months, yearly, or a combination thereof.

In another aspect, the extract is for use when a sign of cancer relapse is observed.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which:

FIG. 14A shows mortality by prostate cancer; FIG. 14B shows average serum PSA levels; and FIG. 14C shows the presentation of undetectable levels of PSA (less than 0.04 ng/ml) after 7 years' follow up.

DETAILED DESCRIPTION OF THE INVENTION

Figure 1:
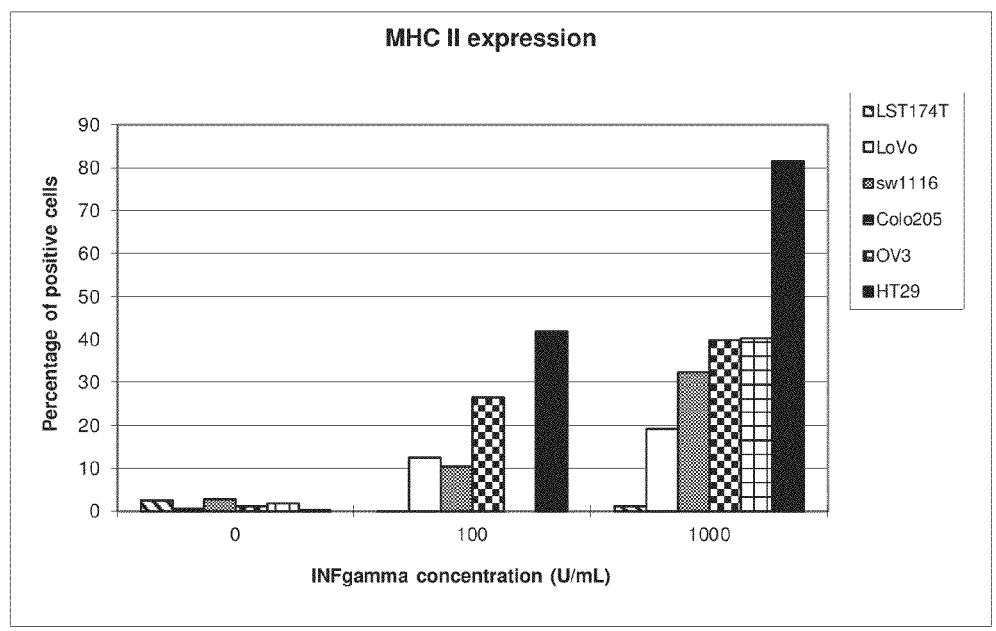
FIG. 1 shows the percentage of MHCII positive cancer cells from various cells lines after a 72 hour incubation period with different amounts of IFN-γ.

In an aspect, the present invention is directed to isolated immunogenic cancer cells, immunogenic compositions and vaccines comprising the immunogenic cancer cells, methods of making such immunogenic compositions and vaccines, and methods for the treatment of cancer. The isolated immunogenic cancer cells are altered or modified so that they present a non-self antigen in the context of MHCII on their surface, so that the MHCII will present the non-self antigen to helper T cells, leading to cytokine production. The isolated immunogenic cancer cells also express MHCI on their cell surface, which presents cancer antigens to cytotoxic T cells. Unexpectedly, a single modified cancer cell can thereby activate both types of T cells in an autologous subject, leading to a strong and specific anti-cancer immune response.

Cancers arise from multiple mutations that lead to several malignant characteristics, such as uncontrolled proliferation, loss of apoptotic mechanisms, and ability of the cancer cells to invade host tissues and metastasize to distant sites. Additionally, although cancer cells frequently express tumour-specific antigens in the context of MHCI on their cell surface that are recognized as non-self by CD8+ cytotoxic T cells, the cancer cells often develop the ability to evade the host immune system. Different mechanisms are present by which cancer cells can evade the immune system, such as:

a) MHCI may be down-regulated on cancer cells, such that the cancer cells cannot be recognized by cytotoxic T cells.

b) The cancer cells may lose expression of the tumour-specific antigens that were recognized as non-self and capable of eliciting an immune response.

c) The cancer cells may fail to induce cytotoxic T cells because they do not express costimulators or MHCII molecules.

d) The cancer cells may produce molecules that suppress an anti-cancer immune response.

e) Certain tumour antigens may induce a specific immune tolerance to the cancer cells.

Methods of enhancing or reinstating an anti-cancer immune response have been the subject of much research in the field of cancer immunology.

MHCII molecules are needed for the activation of CD4+ helper T cells, which stimulate de-differentiation of cytotoxic T cells. Therefore, the induction of cancer-specific T cell responses often requires cross-priming by professional APCs, which express costimulators and MHCII molecules. If such APCs do not adequately take up and present tumour-specific antigens and activate helper T cells, cytotoxic T cells specific for the cancer cells may not develop.

Evidence suggests that antigen-induced T cell proliferation is regulated primarily by the action of interleukin-2 (IL-2) on its specific cell surface receptor. Once helper T cells are stimulated to secrete IL-2, the soluble IL-2 can interact with the cell from which it was produced in an autocrine fashion, or it can interact with other cells that express IL-2 receptors in a paracrine fashion. Accordingly, antigen-activated helper T cells that produce IL-2 can promote their own clonal expansion, promote the expansion of cytotoxic T cells, promote the production of memory T cells, and promote the production of B cells and natural killer (NK) cells. In naïve cytotoxic T cells, the amount of IL-2 produced is typically at least 10 fold less than that produced by helper T cells, and this amount is usually insufficient to sustain an immune response, which is why costimulation by helper T cells is important.

Thus, in order to fully activate the immune system in response to cancer, a four cell interaction model is generally required: 1) the cancer cell, presenting a tumour-specific antigen in the context of MHCI, wherein the antigen is recognized as non-self; 2) an APC, presenting a tumour-specific antigen in the context of MHCII, wherein the antigen is recognized as non-self; 3) a cytotoxic T cell to interact with the MHCI-antigen complex; and 4) a helper T cell to interact with the MHCII-antigen complex. In this model, the recognition of the MHCI-antigen complex by a cytotoxic T cell activates the cytotoxic T cell to a state whereby it requires IL-2 for expansion and prevention of tolerance induction. IL-2 is efficiently provided by activated helper T cells in close proximity to the cytotoxic T cells. Tumour cells often evade the immune system due to a deficiency in this four cell interaction model, typically in that there are insufficient APCs in close proximity to the tumour cells that would present a non-self antigen in the context of MHCII to helper T cells. Thus, helper T cells are not activated and IL-2 is not produced.

In aspects of the present invention, the four cell model is replaced by a three cell model, whereby the cancer cells are themselves modified to present a non-self peptide in the context of MHCII to helper T cells and therefore effectively replace the function of APCs. The modified cancer cells are considered bifunctional, because they will also present a tumour-specific antigen in the context of MHCI to cytotoxic T cells.

In aspects of the present invention, cancer cells are isolated from a subject with cancer and cultured. The cells are modified so as to express MHCII at their cell surface, such as through treatment with an MHCII-inducing agent, such as, for example, IFN-γ. The cells that have been identified as being MHCII-positive are then incubated with an immunogenic non-self antigen, such as, for example, a bovine peptide. During incubation, the non-self antigen will be pinocytosed by the cancer cells, processed, and finally presented on the cell surface in the context of MHCII. The modified cancer cells are then prepared for injection back into an autologous subject, meaning the subject from whom they were originally isolated.

Such modified cells are immunogenic and will produce a strong helper T cell response against the non-self peptide, leading to IL-2 production by the helper T cells. Meanwhile, cytotoxic T cells that have recognized the tumour antigen presented on the cancer cells in the context of MHCI will be stimulated by the IL-2, as they will be in close proximity to the helper T cells, since both MHCI and MHCII are on the surface of the same cancer cells. This will lead to a specific immune response against the tumour antigen produced by the cancer cells. As numerous different tumour antigens are typically presented by MHCI on the surface of the cancer cells, the immune response generated by the modified cancer cells is often polyclonal in nature.

Definitions:

The terms "isolate", "isolated", and "isolating" as used herein refer to removing cancer cells from the body of a patient afflicted with cancer. The cells may be isolated during a standard biopsy procedure or during surgical removal of the cancer, for example. Unless otherwise specified, these terms do not mean that the cancer cells are purified or free from other cell types.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The terms "therapeutically effective amount", "effective amount" or "sufficient amount" mean a quantity sufficient, when administered to a subject, including a mammal, for example a human, to achieve a desired result, for example an amount effective to treat cancer. Effective amounts of therapeutic agents may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the cancer vaccine, the responsiveness of the patient to the cancer vaccine, or a combination thereof. It will also be appreciated that the effective dosage of the cancer vaccine used for the treatment may increase or decrease over the course of a particular treatment regime. Changes in dosage may result and become apparent by standard diagnostic assays known in the art. The cancer vaccine of the present invention may, in aspects, be administered before, during or after treatment with conventional anti-cancer agents, radiotherapy, hormone therapy, biotherapy, and/or surgical tumour resection.

The term "subject" as used herein refers to any member of the animal kingdom, preferably a mammal. In one embodiment, the mammal is a dog, a cat, a hamster, a mouse, a rat, a pig, a horse, cattle or a human being. In another embodiment, the mammal is a human being.

The term "autologous" refers to cells obtained from a subject and used to treat that same subject.

The term "self antigen" or "self peptide" refers to an antigen within the body of a subject that is derived from that specific subject and is usually tolerated by the immune system. The term "non-self antigen" or "non-self peptide" refers to an antigen within the body of a subject that is not derived from that specific subject and is usually identified and attacked by the immune system. A "cancer antigen" or "cancer peptide" refers to an antigen within the body of a subject that is derived from a cancer within the subject. As is understood in the art, cancer antigens are sometimes tolerated by the immune system and are sometimes identified and therefore attacked by the immune system. It will be understood that each cancer cell will present many different cancer antigens in the context of MHCI on its cell surface at any given time, some of which may be tolerated by the immune system and some of which may be identified and attacked by the immune system.

The cancer cells of the invention may be referred to as "bifunctional", because they express both MHCI and MHCII and are capable of activating both helper T cells and cytotoxic T cells, as will be described. These bifunctional tumour cells, expressing MHCI and MHCII, can also be described as tumour presenting cells (TPCs).

The term "adjuvant" refers to a compound or mixture that is present in a vaccine and enhances the immune response to an antigen present in the vaccine. For example, an adjuvant may enhance the immune response to a polypeptide present in an autologous cancer cell vaccine as contemplated herein, or to an immunogenic fragment or variant thereof as contemplated herein. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from Quillay saponaria, the TL4 ligand, a monophosphoryl lipid A, together in a lipid or liposomal carrier. Other adjuvants include, but are not limited to, nonionic block co-polymer adjuvants (e.g., CRL 1005), aluminum phosphates (e.g., $AIPO_4$), R-848 (a Th1-like adjuvant), imiquimod, PAM3CYS, poly (I:C), loxoribine, BCG (bacille Calmette-Guerin) and Corynebacterium parvum, CpG oligodeoxynucleotides (ODN), cholera toxin derived antigens (e.g., CTA 1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

The term "purified" is used herein to encompass compositions that are obtained from a starting material by one or more purification steps that enhance the concentration of the active agent relative to the starting material. For example, in aspects of the present invention, IFN-γ-treated cells obtained from a biopsy or surgical tumour sample may be purified by cell-sorting techniques to provide an increased concentration of MHCII positive cells. The purified composition may contain, for example, from about 5% to about 100% MHCII positive cells, and any amount in between, such as about 10%, about 20%, about 30%, about 40%, about 50%, about 60%, about 70%, about 80%, or about 90% MHCII positive cells. The term "purified" also encompasses compositions that contain a significant quantity of active agent in relation to impurities, whether obtained by a purification process or not. The term "purified" should not be construed to connote absolute purity.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Unexpectedly, it has now been shown that cancer cells can be modified so as to express MHCII on their cell surface, such that the MHCII presents a non-self antigen to helper T cells and MHCI presents a cancer antigen to cytotoxic T cells of the immune system. Cancer cells thus modified are immunogenic and can be used in an autologous cancer vaccine composition that is effective for treating cancer in the subject.

Accordingly, there is therefore provided isolated immunogenic cancer cells that express both MHCI and MHCII on its cell surface, wherein a cancer antigen is bound to said MHCI and a non-self antigen is bound to said MHCII.

The cancer cells are isolated from an autologous subject, meaning that they will be used to treat the same subject from whom they were derived. Alternatively, the cancer cells could be used in an HLA-matched heterologous subject. Typically the cells are isolated during a biopsy procedure or during surgical tumour removal. The cancer cells may be derived from any type of malignancy and, in an aspect, they are derived from lung cancer, including small cell lung cancer and non-small cell lung cancer (e.g. adenocarcinoma), pancreatic cancer, colon cancer (e.g. colorectal carcinoma, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemia (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcoma, liposarcoma, gastrointestinal stromal sarcoma, malignant peripheral nerve sheath tumour (MPNST), Ewing sarcoma, leiomyosarcoma, mesenchymal chondrosarcoma, lymphosarcoma, fibrosarcoma, rhabdomyosarcoma, melanoma, teratocarcinoma, neuroblastoma, brain tumours, medulloblastoma, glioma, benign tumour of the skin (e.g. keratoacanthoma), breast carcinoma (e.g. advanced breast cancer), kidney carcinoma, nephroblastoma, ovary carcinoma, cervical carcinoma, endometrial carcinoma, bladder carcinoma, prostate cancer, including advanced disease and hormone refractory prostate cancer, testicular cancer, osteosarcoma, head and neck cancer, epidermal carcinoma, multiple myeloma (e.g. refractory multiple myeloma), or mesothelioma. In an aspect, the cancer cells are derived from a solid tumour. Typically, the cancer cells are derived from a breast cancer, colorectal cancer, melanoma, ovarian cancer, pancreatic cancer, gastric cancer, or prostate cancer. More typically, the cancer cells are derived from a prostate cancer.

While most cancer cells do not naturally express much if any MHCII on their cell surface, it will be understood that if the cancer cells are derived from antigen-presenting cells, such as a B cell cancer for example, these cells may already express MHCII on their cell surface. It is contemplated that unmodified cancer cells that already express MHCII could be explicitly excluded from the present invention. In other words, it is contemplated that the present invention could encompass cancer cells that are MHCII-negative, MHCII-positive, or both prior to modification according to the present invention. Alternatively, such cells could be included in the invention and it will be understood that, since these cells already express MHCII, incubation with an MHCII-inducing agent is merely optional in order to increase the level of expression.

In order for the cancer cells to express MHCII on their cell surface, they are incubated with an MHCII-inducing agent. An MHCII-inducing agent encompasses, for example, cytokines, chemical agents, and gene constructs.

For example, the MHCII-inducing agent may be IFN-γ, or it may be an MHCII expression vector that is used to transfect or transduce the cancer cells. The MHCII-inducing agent also encompasses a cell expressing MHCII, in that cells that express MHCII could be fused via cell fusion with the cancer cells to render the cancer cells MHCII positive. Examples of such cells include B cells, dendritic cells, macrophages, and monocytes. In another aspect, the MHCII inducing agent may be an agent that activates the MHCII transactivator (CIITA) sequence. Typically, however, the MHCII-inducing agent is a cytokine, such as, for example, IFN-α, IFN-β, IFN-γ, IL-4, IL-13, IL-23, or TNF-α. Combinations of cytokines may also be used. In a specific aspect, the MHCII-inducing agent is IFN-γ. It is understood that the MHCII-inducing agent may also have effects on increasing expression of MHCI on the cancer cells. For example, if IFN-γ is used as the MHCII-inducing agent, it would also tend to cause an increase in MHCI on the surface of the cancer cells.

After incubation with an MHCII-inducing agent, the isolated cancer cells may be screened by conventional methods in order to confirm that MHCII is being expressed on the cell surface. The cells may also be purified at this stage so as to increase the concentration of MHCII-positive cells.

Once the cancer cells are modified so as to express MHCII, they are incubated with a non-self antigen so that they will present the non-self antigen in the context of MHCII. The non-self antigen can be any antigen that is considered non-self and is capable of inducing an immune response in a subject when presented by MHCII. It will be understood that suitable antigens include antigens that are known to be useful as hapten carriers, such as, for example, thyroglobulin, 13-galactosidase, dextran, polylysine, tuberculin derived protein, ovalbumin (OVA), serum albumins such as bovine serum albumin (BSA), sheep serum albumin, goat serum albumins, or fish serum albumin, and keyhole limpet hemocyanin (KLH). The antigen may be derived from the same species as the subject or from a different species. For example, if the subject is a human, the antigen may be a human or non-human antigen. Typically, the antigen is a non-human antigen, such as a bovine, rabbit, murine, canine, or feline antigen, for example. More typically, the antigen is a bovine antigen, such as, for example, bovine serum antigen (BSA). KLH and albumin are other typically used antigens. In an aspect, bovine antigens in general are specifically excluded from the present invention. In another aspect, only BSA is specifically excluded from the present invention.

In aspects, the isolated immunogenic cancer cells prepared according to the invention will express both MHCI and MHCII on their cell surface. The MHCI and MHCII molecules will present a number of different antigens as is understood in the art, however, at least some of the MHCI molecules will present tumour-specific antigens and at least some of the MHCII molecules will present non-self antigens. These cells may be then used in an autologous subject for treatment of cancer in the subject.

The cells may be used live, attenuated, or killed. Typically, the cells are killed prior to use in a subject by, for example, lethal irradiation, freezing and thawing in the absence of a cryo-preservation agent such as DMSO, or treatment with a cytotoxic compound, such as chemotherapy agents or toxins. If the cells are not for immediate use, they can be preserved, such as, for example, by cryo-preservation, for later administration to the autologous subject.

Extracts of the cells may also be used in an autologous subject for treatment of cancer in the subject. For example, the cells may be macerated, sonicated, or otherwise broken up so that they are not in their native whole form. Membrane fractions containing the non-self antigen-bound MHCII molecules may be extracted from the cells and provided in an immunogenic composition for treating cancer in an autologous subject. Additionally, fractions containing just the non-self antigen bound MHCII molecules may be extracted from the cells and provided in an immunogenic composition for treating cancer in an autologous subject. Accordingly, there is therefore provided a cellular extract containing MHCII molecules, wherein the MHCII molecules present a non-self antigen. The extract may further comprise membrane fractions, and it may further comprise MHCI molecules, wherein the MHCI molecules present a cancer antigen. The extract may be provided in an immunogenic composition or a cancer vaccine and may be used to treat an autologous subject with cancer.

Cancer cells modified as described to present a non-self antigen in the context of MHCII can also be used in an immunogenic composition to treat cancer. Accordingly, there is therefore provided a composition comprising cancer cells that express both MHCI and MHCII on their cell surface, said MHCI presenting a cancer antigen and said MHCII presenting a non-self antigen. Such an immunogenic composition finds use as an autologous cancer cell vaccine, for treating cancer in an autologous subject.

In addition to the modified cancer cells, the immunogenic compositions and vaccines may further comprise one or more pharmaceutically acceptable excipients, carriers, buffers, stabilizers, adjuvants, or mixtures thereof.

The immunogenic compositions and vaccines described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions may include, albeit not exclusively, the cancer cells in association with one or more pharmaceutically acceptable vehicles or diluents, and may be contained in buffered solutions with a suitable pH that are iso-osmotic with physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of the subject. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the modified cancer cells, together with a suitable amount of carrier so as to provide the form for direct administration to the patient.

Any suitable adjuvant may be used in the vaccines of the invention. For example, suitable adjuvants include MPL-TDM adjuvant, AS021/AS02, nonionic block co-polymer adjuvants, aluminum phosphates, R-848, imiquimod, PAM3CYS, poly (I:C), loxoribine, BCG, Corynebacterium parvum, CpG oligodeoxynucleotides, cholera toxin derived antigens, lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water, keyhole limpet hemocyanins, and dinitrophenol. Typically, the adjuvant used is BCG.

The immunogenic compositions and vaccines of the invention can, in aspects, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, aerosol or oral administration. Typically, the compositions of the invention are administered subcutaneously, intramuscularly, or intradermally. More typically, the compositions of the invention are administered intradermally in the upper limbs due to the specific antigen processing that occurs in the derma.

The immunogenic compositions and vaccines of the invention may, in aspects, be administered in combination, concurrently or sequentially, with conventional treatments for cancer, including chemotherapy, hormone therapy, biotherapy, and radiation therapy, for example. The compositions of the invention may be formulated together with such conventional treatments when appropriate.

The compositions of the invention may be used in any suitable amount, but are typically provided in doses comprising from about $1 \times 10^4$ to about $1 \times 10^9$ cancer cells. For example, the compositions of the invention may, in aspects, comprise about $1 \times 10^4$, $1 \times 10^5$, about $1 \times 10^6$, about $1 \times 10^7$, about $1 \times 10^8$, or about $1 \times 10^9$ cancer cells. Typically, the compositions comprise about $1 \times 10^7$ cancer cells.

Additionally, vaccination with the cancer cells may occur once or may be repeated several times. For example, vaccination may occur daily, weekly, monthly, yearly, or a combination thereof, depending upon the disease state. For example, a subject may be administered several doses on a weekly basis in order to treat an active cancer. Once the cancer growth slows or goes into remission, follow-up maintenance doses may be provided, for example, on a monthly basis, every three months, every six months, or on a yearly basis. In general, it is desired to continue vaccinating the subject for as long as there is biological material available. Additionally, cancer patients are typically followed for several years after remission in order to quickly identify any signs of cancer relapse. If any such signs are identified, a follow-up dose or doses of the cancer cell vaccine may be administered as needed to treat the relapsing cancer.

It will be understood that the number of doses is only limited by the number of cancer cells obtained from the tumour of the patient. For example, when the cancer cells are isolated from the subject, they are cultured for a period of time to ensure viability and increase cell number. If a predetermined number of doses is desired, the cells may be cultured until a sufficient number of cells is present to prepare the predetermined number of doses. Once all the original cell material is used up, no further doses may be prepared unless a further biopsy or surgical sample is obtained.

It is therefore contemplated that the cancer cells could be cryopreserved after culturing, either prior to or after treatment with the MHCII-inducing agent and the non-self antigen, so that they could be re-cultured and expanded in cell number should further doses be required at a future time, for example, if the cancer relapses. In the specific case of a relapse, a second biopsy or surgical sample from the relapsed cancer could be obtained in order to provide additional biological material for further vaccination doses. If possible, it is desirable to obtain a second biopsy or surgical sample from the relapsed cancer because the relapsed cancer may present different cancer antigens in the context of MHCI than the original cancer.

While it has been stated above that the compositions, vaccines, cells, and methods of the invention can be used to treat cancer, it will be understood that they could also be used to prevent cancer. In this aspect, tumour cells obtained from a subject can be screened to determine which human leukocyte antigens (HLAs) are expressed on their surface. These cells can be formulated into a vaccine for preventing cancer in an HLA-matched subject.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Figure 2:
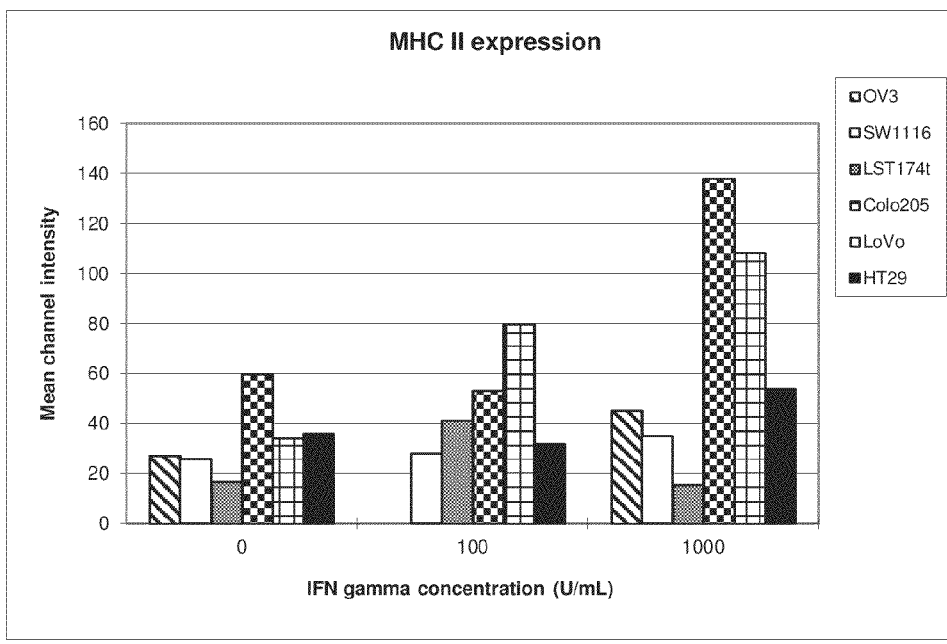
FIG. 2 shows the level of MHCII expression on MHCII positive cancer cells from various cell lines after a 72 hour incubation period with different amounts of IFN-γ.

Human LST174T, LoVo, SW1116, Colo205, and HT29 colon cancer cells and human SK-OV-3 ovarian cancer cells were cultivated with varying concentrations of IFN-γ for 72 hours. The cells were then analyzed by flow cytometry using a specific anti-MHCII (DP, DQ and DR) antibody in order to determine whether IFN-γ induced MHCII expression in these cells. The results are shown in Tables 1 and 2 and corresponding FIGS. 1 and 2.

TABLE 1

This table lists the percentage of MHCII positive cells following a 72 hour incubation with IFN-γ.

| IFN-γ (U/mL) | LST174T | LoVo | SW1116 | Colo205 | OV3 | HT29 |
|---|---|---|---|---|---|---|
| 0 | 2.70 | 0.59 | 2.96 | 1.35 | 2.03 | 0.35 |
| 100 | 0.26 | 12.41 | 10.50 | 26.59 | NA | 41.87 |
| 1000 | 1.32 | 19.11 | 32.54 | 39.96 | 40.43 | 81.60 |

TABLE 2

This table lists the mean channel intensity and relates to the level of expression of MHCII on MHCII positive cells.

| IFN-γ (U/mL) | LST174T | LoVo | SW1116 | Colo205 | OV3 | HT29 |
|---|---|---|---|---|---|---|
| 0 | 16.7 | 34.29 | 25.71 | 59.89 | 27.14 | 35.87 |
| 100 | 41.42 | 79.86 | 27.88 | 53.28 | NA | 31.91 |
| 1000 | 15.68 | 108.43 | 34.91 | 138.24 | 45.32 | 53.76 |

This example shows that several different cell types of different origins can be made to express MHCII following incubation with IFN-γ.

Example 2

Mouse 413-BCR mammary tumour cells were incubated for 48 hours with 100 U/mL IFN-γ and for 24 hours with 50 μg/mL BSA. More specifically, the cells were placed in T25 flasks with 10 ml of medium. The cells were incubated for 48 hours with the medium containing the IFN-γ then were washed with serum-free RPMI 1640 three times. The cells were then incubated with 2 ml of the BSA solution for 2 hours, then complete medium was added, including 100 U/ml IFN-γ and 50 μg/ml BSA. The 413-BCR cells were lehally irradiated and cryopreserved. BALB/c mice were pre-immunized with 3 injections, each containing $1 \times 10^5$ 413-BCR cells, administered i.p. with no adjuvant, on days 21, 14, and 7 before challenge. The mice were then challenged with an s.c. injection of $2.5 \times 10^6$ viable 413-BCR cells. All pre-immunized mice failed to develop tumours (n=5), whereas all untreated control mice (n=5) developed tumours after 30 days.

This example shows that pre-immunizations with cancer cells modified to present a non-self peptide in the context of MHCII on their cell surface was protective against challenge with autologous non-modified cancer cells in mice.

Example 3

20 BALB/c female mice were divided into four groups of five mice each, labeled A, B, C, and D. These mice received two pre-immunizations as set out below in Table 3. Briefly, group A was immunized with cancer cells presenting non-self antigen in the context of MHCII on their cell surface; group B was immunized with cancer cells expressing MHCII on their cell surface without non-self antigen; group C was immunized with non-self antigen; and group D was immunized with PBS. All injections were performed s.c. and included Quil-A as an adjuvant on Day 14 before challenge and no adjuvant on day 7 before challenge. On day 0, $5 \times 10^5$ viable 413-BCR cells were injected s.c.

TABLE 3

This table sets out the pre-immunizations that the groups of mice in Example 3 received.

| Treatment | Procedure |
|---|---|
| A | $10^5$ 413-BCR cells, incubated with 100 U/ml IFN-γ for 48 h followed by incubation with 50 ug/ml BSA and 100 U/ml IFN-γ for 24 hours. The cells were lethally irradiated. |
| B | $10^5$ 413-BCR cells, incubated with IFN-γ for 72 h. The cells were lethally irradiated. |
| C | 50 ug BSA |
| D | PBS |

Figure 3:
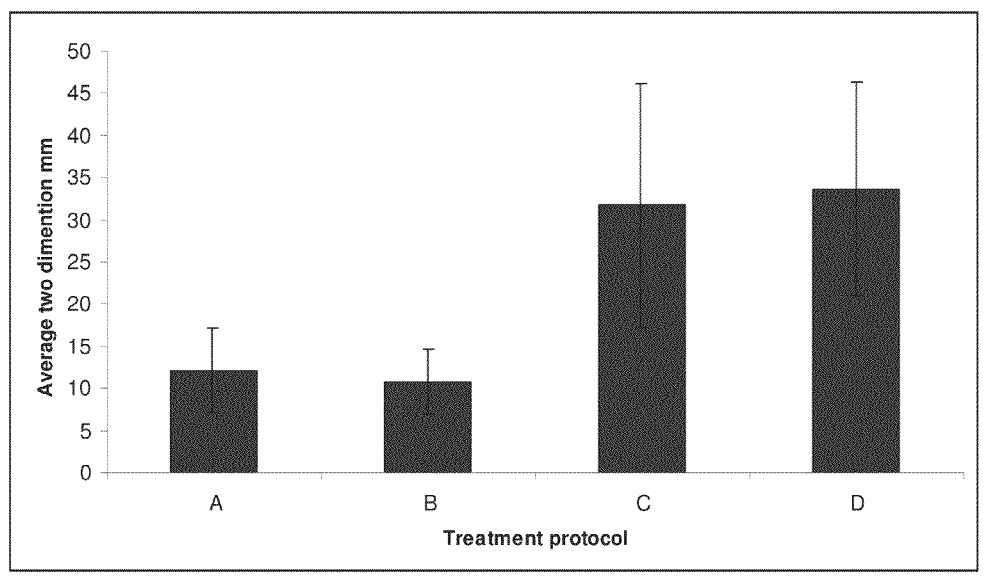
FIG. 3 shows the 2-dimensional average tumour size and standard deviation of tumours in control mice or mice immunized with the autologous cancer cell vaccine 30 days after challenge with viable cancer cells.
Figure 4:
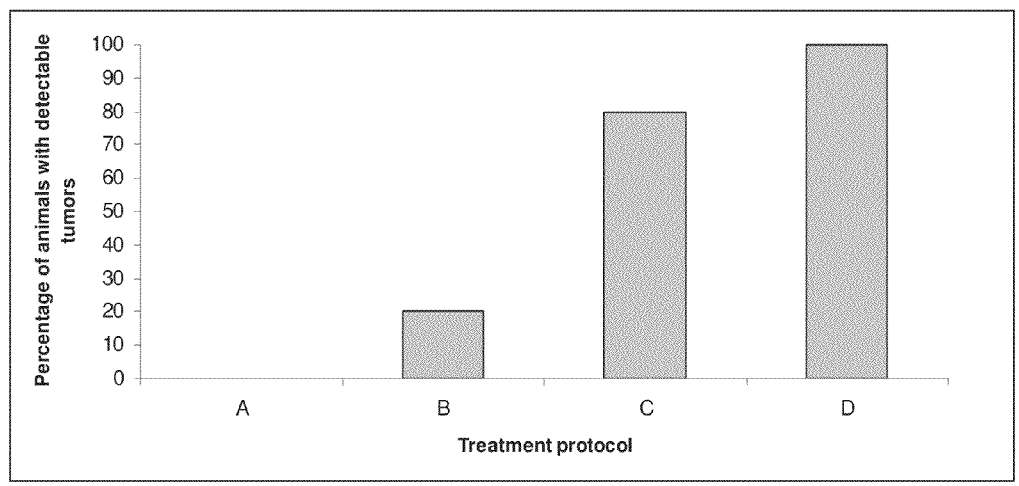
FIG. 4 shows the incidence of detectable tumours in control mice or mice immunized with the autologous cancer cell vaccine 30 days after challenge with viable cancer cells.

Table 4 and FIGS. 3 and 4 set out the results of this study. Table 4 and corresponding FIG. 3 show that mice from Groups A and B, which received MHCII-expressing cancer cells in their pre-immunizations, had tumour sizes that were smaller than the tumour sizes of the mice that did not receive cells in their pre-immunizations. Macroscopic evaluation of the mice on day 70 revealed that no mice of group A had detectable tumours, whereas groups B, C, and D had 1, 4, and 5 of 5 mice, respectively, with detectable tumours (FIG. 4).

TABLE 4

This table shows the two-dimensional average tumour size and standard deviation amongst the mice in each group, 30 days after challenge with viable tumour cells.

| | Two dimensional tumour size on day 30 | |
|---|---|---|
| | Average (mm²) | SD (mm²) |
| A | 12.1 | 5.1 |
| B | 10.8 | 3.8 |
| C | 31.7 | 14.4 |
| D | 33.7 | 12.7 |

This example shows that pre-immunizations with cancer cells modified to present a non-self peptide in the context of MHCII on their cell surface was protective against challenge with autologous non-modified cancer cells in mice, specifically in terms of a reduction in tumour size and incidence.

Example 4

The mice from group A of Example 3 were sacrificed and their spleens were removed to perform a T cell proliferation assay. Spleens from naïve animals were used as a control. Approximately $1.2 \times 10^5$ T cells/well from the mice of group A were cultured in the presence of the following agents or cells: 2 mg/mL phytohemagglutinin (PHA) (positive control); standard medium (negative control); $10^4$ irradiated tumor cells, $10^4$ irradiated IFN-γ-treated tumor cells, or 50 μg/mL BSA. The T cells were incubated at 37° C. for 48 hours followed by a 20 hour incubation with 1 mCi 3H-thymidine. The incorporated activity was measured using solid scintillation.

Figure 5:
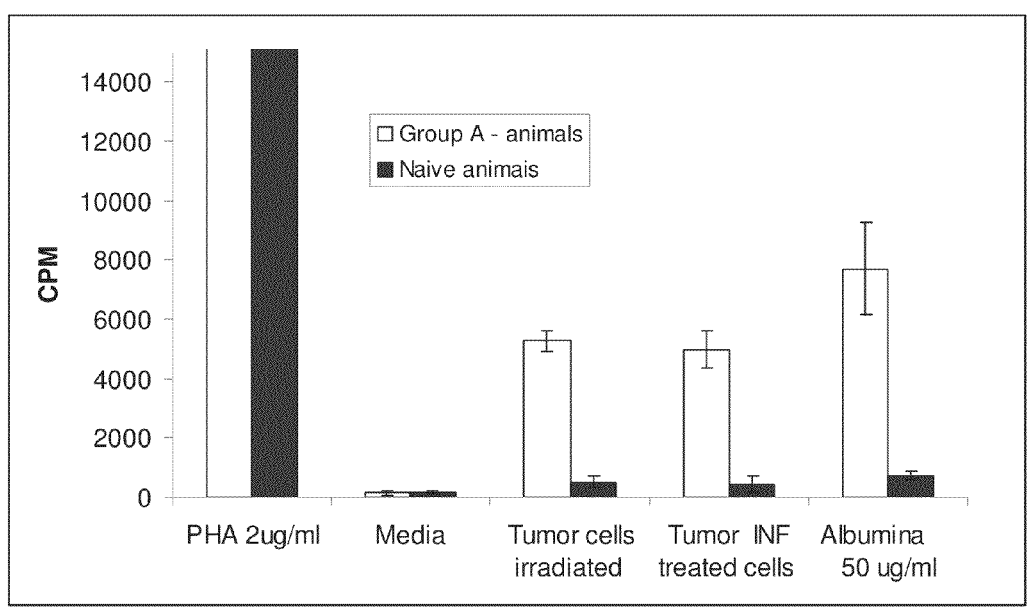
FIG. 5 shows the T cell proliferative responses in T cells obtained from immunized or naïve mice after incubation with tumour cells.

Table 5 and FIG. 5 show the results of this study and indicate T cells derived from the immunized mice proliferated in response to tumour cells and BSA, whereas T cells derived from naïve mice did not. This means that the animals immunized with the cancer vaccine developed independent immunity towards the different tumour antigens present on the tumour cells, regardless of whether those cells were treated with IFN-γ or not. Additionally, the animals immunized with the cancer vaccine indicated immunity towards BSA.

TABLE 5

This table shows the proliferative response of T cells from immunized (group A) versus naïve mice.

| | Group A - Immunized Animals | | Naïve Animals | |
|---|---|---|---|---|
| | Media CPM | DP CPM | Media CPM | DP CPM |
| PHA 2 ug/ml | 145659 | 4718 | 143239 | 10850 |
| Media | 138 | 60 | 157 | 71 |
| Tumor cells irradiated | 5268 | 372 | 506 | 184 |
| Tumor INF treated cells | 4989 | 638 | 430 | 262 |
| Albumina 50 ug/ml | 7714 | 1555 | 735 | 159 |

Example 5

Figure 6:
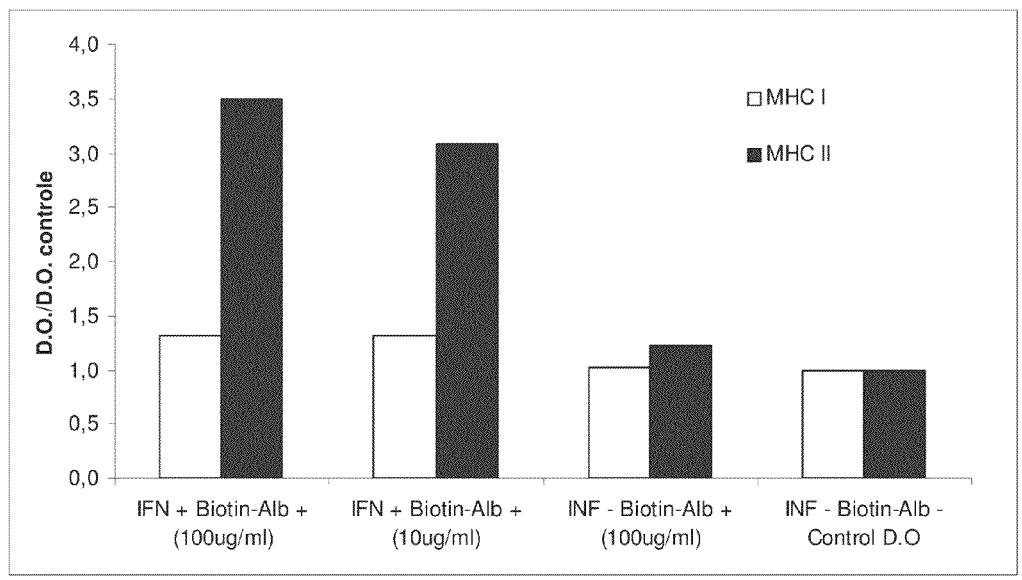
FIG. 6 shows MHCII presenting BSA-biotin peptides extracted from cells treated with IFN-γ.

$10^6$ 413-BCR cells were incubated with 100 U/ml IFN-γ for 48 h. The cells were washed 5 times with PBS and were then incubated with 100 μg/ml or 10 μg/ml (2 ml) of biotin-BSA for 2 hours, using a high biotin molar ratio (1 mole of BSA to 20 moles of biotin). The cells were then incubated in medium containing IFN-γ plus biotin-BSA for 24 hours. The cells were washed 5 times with PBS and solubilized with Triton-100™ overnight. Anti-mouse MHCI or MHCII (10 ug/ml in PBS) capture antibodies were coated on a 96 well ELISA plate. The plate was blocked with BSA at 3% in PBS for 1 hour. Samples containing solubilized cells were incubated for 4 hours at room temperature. The plates were washed and streptavidine-peroxidase conjugate was added for 45 minutes at 37° C. Plates were then washed 5 times and a TMB substrate added. The optical density was determined at 450 nm. The ratio between the control sample (untreated cells) and the treated cells is shown in FIG. 6.

This example shows that BSA is capable of binding to MHCII expressed by cancer cells pre-treated with IFN-γ in a dose-dependent manner.

Example 6

A group of SCID-beige mice, reconstituted with human PBLs, were reconstituted for the in vivo evaluation of the autologous cancer vaccine described herein. More specifically, twenty-five SCID-beige mice (female, 8-10 weeks,) were injected with $10^7$ hPBLs from a partial match donor (HLA type A2, B44, DR13) i.p. (0.5 mL/mouse with 20% v/v Matrigel). Mouse blood was collected 7 and 14 days after reconstitution to verify hIgG levels. Only mice with hIgG greater than 10 ug/mL were utilized for further experiments. Table 6 shows the hIgC measurements of the reconstituted mice.

TABLE 6

This table shows the hIgG measurements of the reconstituted mice and sets out which mice were used for further study and which were not.

| | h-IgG ug/ml | | |
|---|---|---|---|
| Mouse | Day 7 | Day 14 | |
| 1-1 | 0 | 15.6 | reconstituted |
| 1-2 | 0 | 1919.7 | reconstituted |
| 1-3 | ND | 560 | reconstituted |
| 1-4 | ND | 211.2 | reconstituted |
| 1-5 | ND | 26.4 | reconstituted |
| 2-1 | 0 | 407.9 | reconstituted |
| 2-2 | 0 | 338.6 | reconstituted |
| 2-3 | ND | 99.2 | reconstituted |
| 2-4 | ND | 19.4 | reconstituted |
| 2-5 | ND | 3.4 | Deleted |
| 3-1 | 0 | 37.8 | reconstituted |
| 3-2 | 0 | 120.5 | reconstituted |
| 3-3 | ND | 10.2 | reconstituted |
| 3-4 | ND | 229.6 | reconstituted |
| 3-5 | ND | 7.3 | Deleted |
| 4-1 | 0 | 12.2 | reconstituted |
| 4-2 | 0 | 1.7 | Deleted |
| 4-3 | ND | 0 | Deleted |
| 4-4 | ND | 2.3 | Deleted |
| 4-5 | ND | 384.7 | Reconstituted |
| 5-1 | 0 | 0 | Deleted |
| 5-2 | 0 | 13.2 | reconstituted |
| 5-3 | ND | 1396.5 | reconstituted |
| 5-4 | ND | 5.4 | Deleted |
| 5-5 | ND | 3.6 | Deleted |

ND, not determined 17 (68%) of the SCID-Beige mice were reconstituted by day 14. These animals are then used for in vivo evaluation of the autologous cancer vaccine. These mice were randomly divided into four groups for immunizations as follows:

A) N=5, $10^6$ irradiated modified tumor cells, wherein the tumor cells were modified by treatment with 100 U/ml IFN-γ for 48 hours plus 50 ug/ml BSA for 24 hours as described above;
B) N=4, $10^6$ irradiated modified tumor cells, wherein the tumor cells were modified by treatment with IFN-γ for 72 hours;
C) N=4, 100 ug/mouse BSA; and
D) N=4, PBS.

The tumour cells used for immunization and challenge were from the cell line SW 1116 (HLA type A2, 23, B 44,60, DR 11,13,52, DQ 6,7). The immunization protocol is set out in Table 7. All groups were immunized i.p. with Ribi adjuvant. RiBi was used only in the first immunization due to its toxicity.

TABLE 7

This table sets out the immunization and challenge protocol used in this in vivo model.

| Day | Procedure |
|---|---|
| −14 | Immunization |
| −7 | Immunization |
| 0 | Tumor implantation - 2.5 × $10^6$ SW 1116 cells, s.c. |
| +3 | Immunization |
| +8 | Immunization |
| +15 | Immunization |

Figure 7:
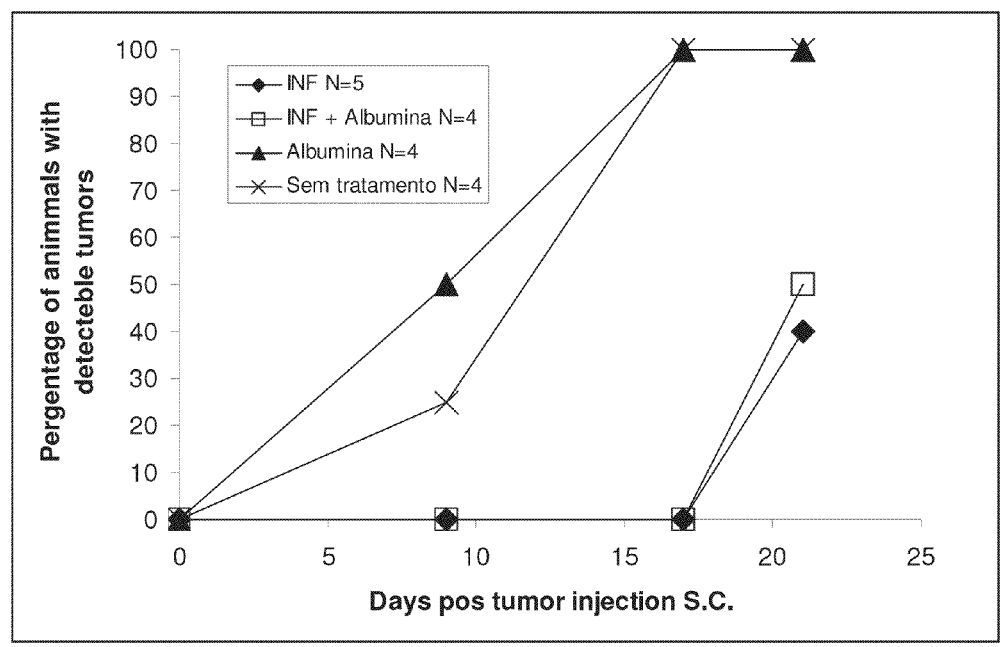
FIG. 7 shows the incidence of detectable tumours in control mice or mice immunized with the autologous cancer cell vaccine after challenge with viable cancer cells.

The results of this study are set out in Table 8 and FIG. 7. These results show that all mice receiving immunizations with BSA or PBS alone had detectable tumours by 17 days after challenge. In contrast, mice receiving modified cancer cells had no detectable tumours by 17 days after challenge and only 2 of 5 had detectable tumours by day 21 after challenge.

TABLE 8

This table shows tumour incidence in mice vaccinated with the autologous cancer vaccine, as compared to mice vaccinated with control formulations.

| Treatment Group | Day 9 Tumor (N) | Day 17 Tumor (N) | Day 21 Tumor (N) |
|---|---|---|---|
| A (N = 5) | 0 | 0 | 2 |
| B (N = 4) | 0 | 0 | 2 |
| C (N = 4) | 2 | 4 | 4 |
| D (N = 4) | 1 | 4 | 4 |

Example 7

The autologous cancer vaccine was tested in humans. Cells were obtained by surgery or a biopsy procedure. The surgeon collected a small fragment of the tumour (up to about 0.5 cm$^3$) that appeared to contain tumour cells macroscopically. When needle biopsies were used, multiple needle samples were collected. The cells were immediately placed in a tube containing transport medium (RPMI 1640, plus 20% FBS, plus penicillin, plus streptomycin or gentamycin, plus 10 mM oxaloacetic acid, 4.5 mM pyruvate, and 2.0 U/ml insulin (human or bovine)). The collected samples were placed on ice (about 2 to 8° C.) until processed at the cell culture lab 30 minutes to 72 hours after collection. Typically the time between tumour collection and tumour processing was less than about 24 hours. Once the material arrived at the lab, the cells were washed 3 times with cold RPMI 1640 and were mechanically dissociated using glass grinding, scissors, or a scalpel. The cells could also have been enzymatically dissociated using trypsin for example, however, mechanical dissociation was used because it does not interfere with superficial cell membrane proteins. Some tumours presented themselves as ascites fluid or bone marrow samples. In these cases, mechanical dissociation was not required.

The dissociated cells together with some smaller tumour fragments were placed in culture using VAP medium (RPMI 1640, plus 10% FBS, plus penicillin, plus streptomycin or gentamycin, plus 10 mM oxaloacetic acid, 4.5 mM pyruvate, and 2.0 U/ml insulin (human or bovine)). T25 or T75 culture flasks were used. The average time to reach at least 7×10$^7$ cells was 28 days, but ranged from 10 to 91 days in these samples. Medium was replaced every 3 days or when needed, based upon the tumour cell growth characteristics.

Once there were sufficient cells (at least 3 confluent T25 flasks), 1000 IU of IFN-γ was added per ml of fresh VAP medium (7ml) per T25 flask. The cells containing IFN-γ were incubated for 48 hours at 37° C. The cells were then washed 3 times with 5 ml RPMI 1640 and were incubated with 50 μg/ml of BSA in RPMI 1640 at 37° C. The BSA-containing medium was removed and replaced with VAP medium plus 1000 U IFN-γ plus 50 ug/ml of BSA and was incubated for a further 24 hours. After these incubation times, the cells were mechanically harvested using a scraper and were washed 5 times with saline. The washed cells were re-suspended in sterile PBS such that there were at least 1×10$^7$ cells per ml and were placed in a 1 ml micro tube. Each patient sample was evaluated by flow cytometry in order to confirm the presence of MHC I and MHC II, as well as the presence of a surface tumour marker when available.

Samples were then irradiated with 200 Gy radiation. Irradiated cells were then fractionated into 7 or more micro tubes containing 150 pl of cells each (approximately 10$^7$ cells). Tubes containing samples one and two were refrigerated at 2 to 8° C., and the remaining samples were frozen at -80° C. BCG, at 10$^7$ microorganisms, was added (50 ul) so that the final volume for the two first samples was 200 pl (150 pl of cells plus 50 pl of BCG). The samples were then transferred to a tuberculin syringe and injected intradermally in the upper limb. The first two immunizations were performed on different arms with a 7 days interval in between. Previous to the first immunization, blood was collected for humoral and cellular immune response analyses when available.

The third dose of the vaccine contained only irradiated tumour cells diluted in PBS (10$^7$ cells), and was inoculated 7 days after the second dose. The fourth dose was performed in the same way as the third in the alternate arm. The 5$^{th}$ and the 6$^{th}$ doses were performed at 30 days intervals. Finally the 7$^{th}$ dose was administered 3 months after the 6$^{th}$ dose. If biological material was available, subsequent doses were administered every 3 or 2 months depending on patient evolution. Clinical and biochemical evaluation were performed at each dose. Standard cancer treatments were maintained during all the immunization procedure. Delayed-type hypersensitivity (DTH) reactions were measured 24, 48 or 72 hours after each immunization, with the exception of the two initial doses that contained BCG. Vaccines were successfully prepared from many patients and tumour sites, as set out in Table 9.

TABLE 9

This table shows the number of patients and tumour sites from which autologous cancer cell vaccines were successfully prepared.

| Tumor site | Number of patients |
|---|---|
| Prostate | 159 |
| Breast | 7 |
| Intestine | 5 |
| Lung | 5 |
| Cerebral | 3 |
| Gastric | 3 |
| Melanoma | 3 |
| Ovarian | 3 |
| Pancreas | 3 |
| Thyroid | 3 |
| Gallbladder | 3 |
| Cervical Cancer | 2 |
| Liver | 2 |
| Mesothelioma | 2 |
| unknown site | 2 |
| Rectum | 2 |
| Kidney | 2 |
| Sarcoma | 2 |
| Head and Neck | 2 |
| Myeloma | 1 |
| Bladder | 1 |
| Esophagus | 1 |
| Lachrymal Gland | 1 |

Figure 8:
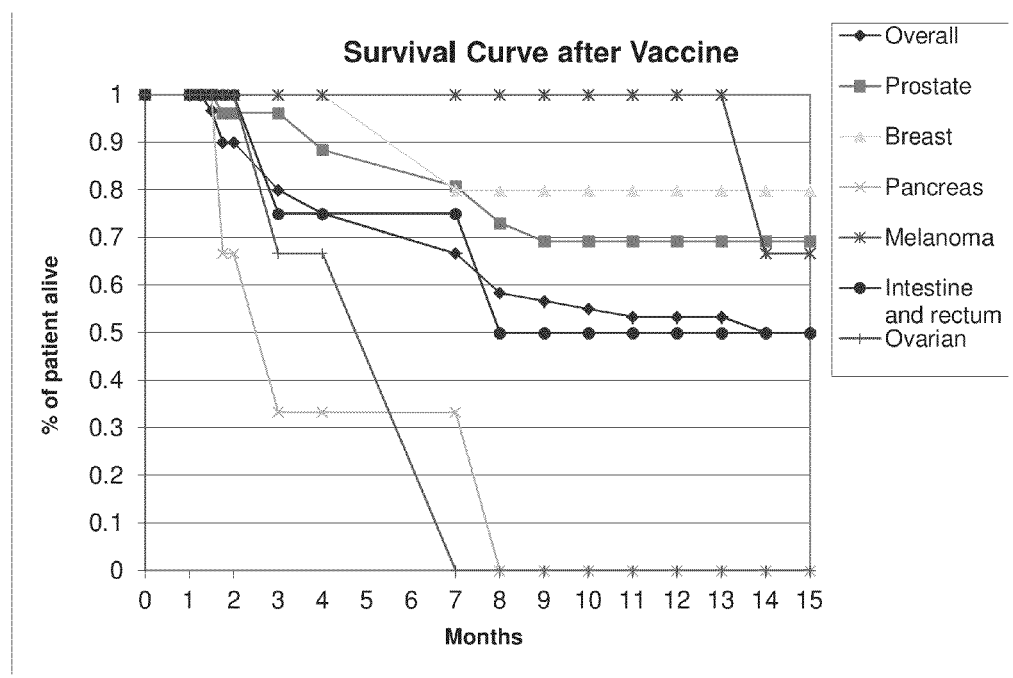
FIG. 8 shows survival curves of human subjects receiving the autologous cancer cell vaccine.

After successful vaccine preparation, the vaccine was used to treat humans and was found to be safe and effective. The results of this study are set out in Table 10 and corresponding FIG. 8.

TABLE 10

This table sets out the percent survival of 60 patients with various cancer types treated with the autologous cancer vaccine.

| Months | 60 Overall | 26 Prostate | 5 Breast | 3 Pancreas | 3 Melanoma | 4 Intestine and rectum | 3 Ovarian |
|---|---|---|---|---|---|---|---|
| 0 | 100% | 100% | 100% | 100% | 100% | 100% | 100% |
| 1 | 100% | 100% | 100% | 100% | 100% | 100% | 100% |
| 1.25 | 100% | 100% | 100% | 100% | 100% | 100% | 100% |
| 1.5 | 97% | 100% | 100% | 100% | 100% | 100% | 100% |
| 1.75 | 90% | 96% | 100% | 67% | 100% | 100% | 100% |
| 2 | 90% | 96% | 100% | 67% | 100% | 100% | 100% |
| 3 | 80% | 96% | 100% | 33% | 100% | 75% | 67% |
| 4 | 75% | 88% | 100% | 33% | 100% | 75% | 67% |
| 7 | 67% | 81% | 80% | 33% | 100% | 75% | 0% |
| 8 | 58% | 73% | 80% | 0% | 100% | 50% | 0% |
| 9 | 57% | 69% | 80% | 0% | 100% | 50% | 0% |
| 10 | 55% | 69% | 80% | 0% | 100% | 50% | 0% |
| 11 | 53% | 69% | 80% | 0% | 100% | 50% | 0% |
| 12 | 53% | 69% | 80% | 0% | 100% | 50% | 0% |
| 13 | 53% | 69% | 80% | 0% | 100% | 50% | 0% |
| 14 | 50% | 69% | 80% | 0% | 67% | 50% | 0% |
| 15 | 50% | 69% | 80% | 0% | 67% | 50% | 0% |

Example 8

Case studies of clinical trials for five patients with prostate cancer are now described and their prostate specific antigen (PSA) measurements before, during, and after vaccination are provided. Vaccine preparation and treatments were as in Example 7.

Figure 9:
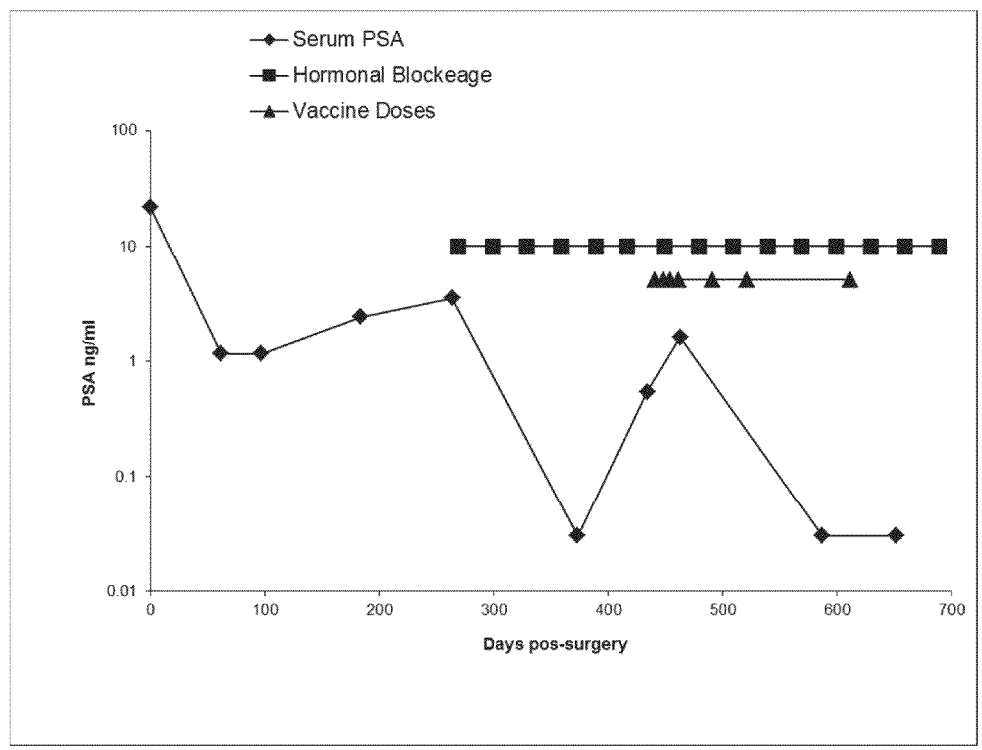
FIG. 9 shows prostate specific antigen (PSA) measurements of Patient 1, receiving the autologous cancer cell vaccine following surgical resection of a prostate tumour and concurrently with hormone blockade therapy.

Patient 1:

Patient 1 was treated with hormone blockade therapy on a monthly basis starting on day 269 post-surgery. A first dose of the autologous cancer vaccine was provided on day 441 and subsequent doses were provided on days 448, 454, 461, 491, 521, and 611. FIG. 9 shows that while hormone blockade initially caused a reduction in PSA levels, as measured at day 373, they began rising again and peaked at day 463. Treatment with the autologous cancer vaccine caused a further sustained reduction in PSA levels in this patient to a low of 0.03 at days 587 and 651.

Figure 10:
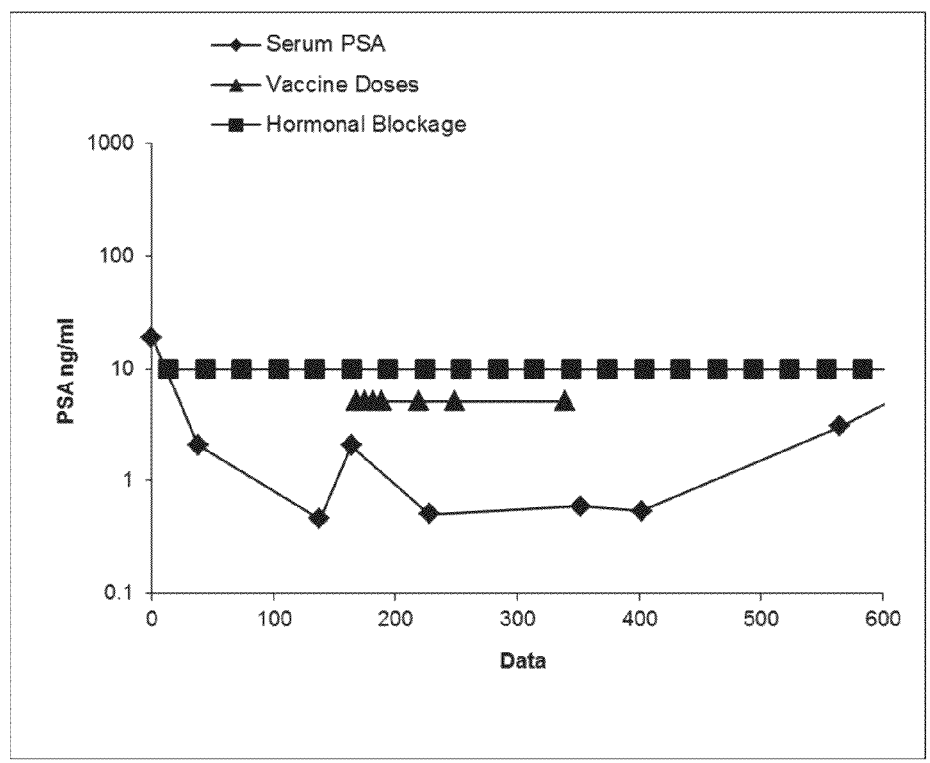
FIG. 10 shows PSA measurements of Patient 2, receiving the autologous cancer cell vaccine following surgical resection of a prostate tumour and concurrently with hormone blockade therapy.

Patient 2:

Patient 2 was treated with hormone blockade therapy on a monthly basis starting on day 14 post-surgery. A first dose of the autologous cancer vaccine was provided on day 168 and subsequent doses were provided on days 175, 182, 189, 219, 249, and 339. FIG. 10 shows that while hormone blockade initially caused a reduction in PSA levels, as measured at day 138, they began rising again and peaked at day 164. Treatment with the autologous cancer vaccine caused a further sustained reduction in PSA levels until day 402, when levels began rising again.

Figure 11:
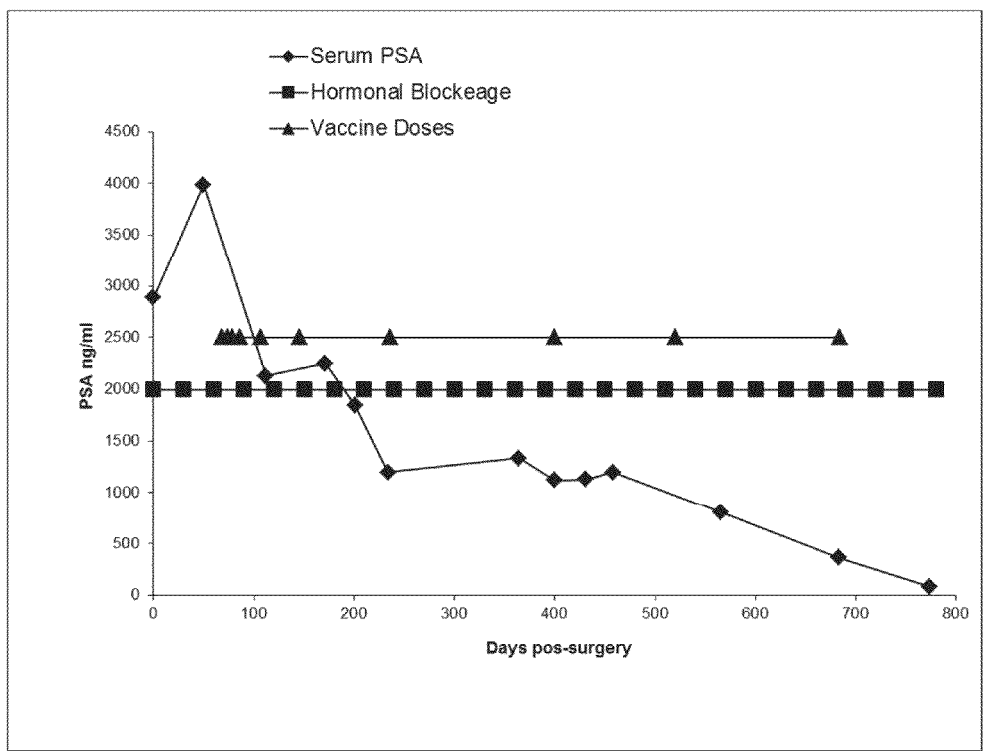
FIG. 11 shows PSA measurements of Patient 3, receiving the autologous cancer cell vaccine following surgical resection of a prostate tumour and concurrently with hormone blockade therapy.

Patient 3:

Patient 3 was treated with hormone blockade therapy on a monthly basis starting 6 months before surgical sample collection. A first dose of the autologous cancer vaccine was provided on day 68 and subsequent doses were provided on days 74, 79, 86, 107, 146, 236, 400, 520, and 684. FIG. 11 shows that, even in a hormone-resistant patient, the combined hormone blockade and vaccination treatment caused a steady reduction in PSA levels in this patient.

Figure 12:
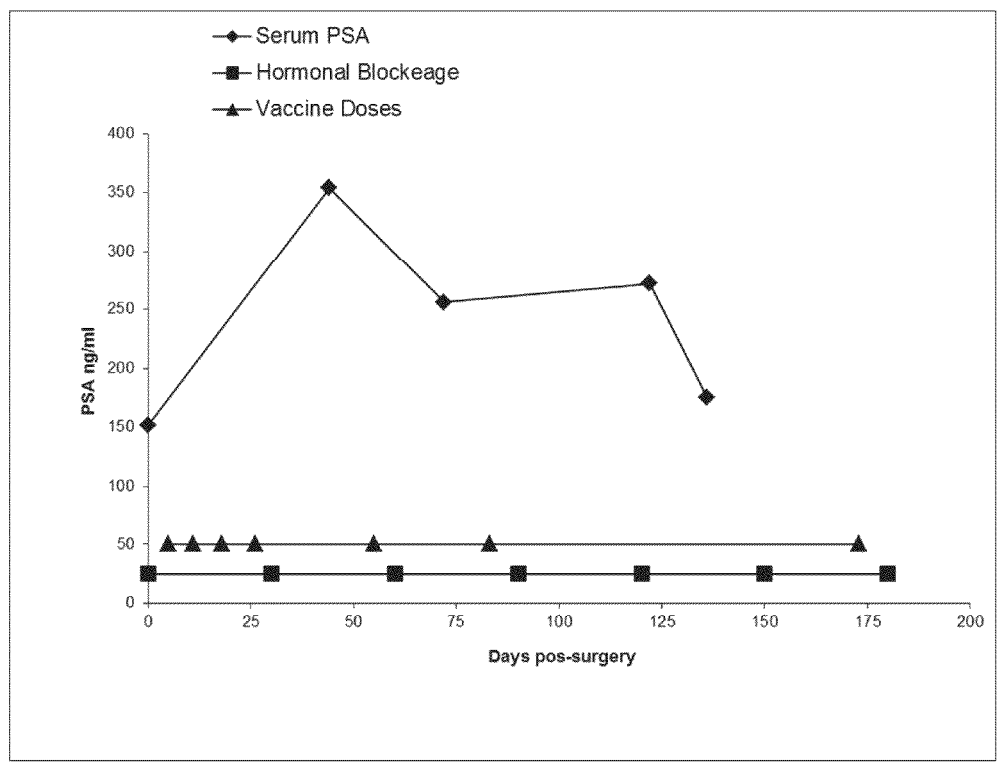
FIG. 12 shows PSA measurements of Patient 4, receiving the autologous cancer cell vaccine following surgical resection of a prostate tumour and concurrently with hormone blockade therapy.

Patient 4:

Patient 4 was treated with hormone blockade therapy on a monthly basis starting on day 0 post-surgery. A first dose of the autologous cancer vaccine was provided on day 5 and subsequent doses were provided on days 11, 18, 26, 55, 83, and 173. FIG. 12 shows that the combined hormone blockade and vaccination treatment caused a reduction in PSA levels in this patient from a high of 354 on day 44 to a low of 175 on day 136, the last day on which a measurement was recorded.

Figure 13:
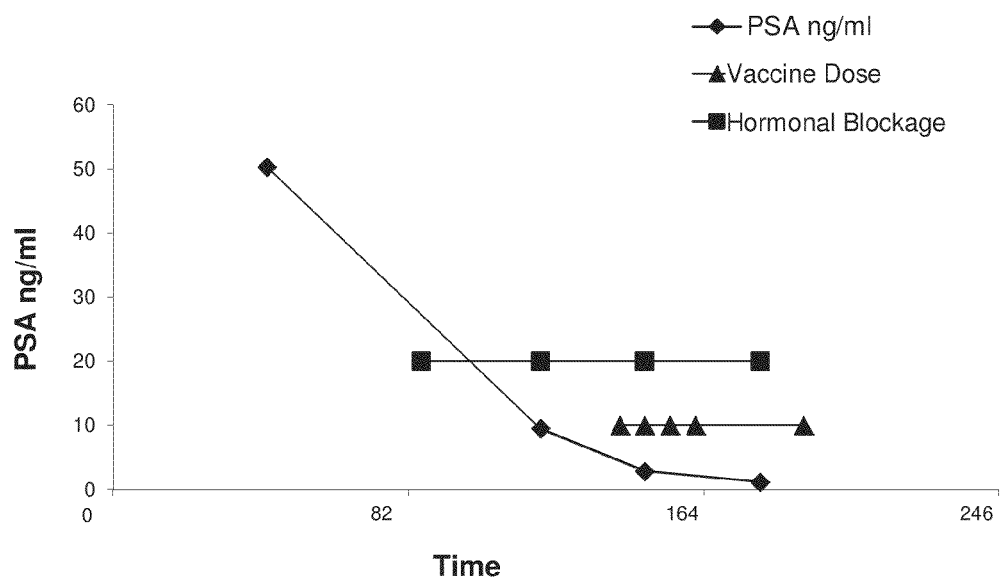
FIG. 13 shows PSA measurements of Patient 5, receiving the autologous cancer cell vaccine following surgical resection of a prostate tumour and concurrently with hormone blockade therapy.

Patient 5:

Patient 5 was treated with hormone blockade therapy on a monthly basis starting just after surgery on approximately day 30. A first dose of the autologous cancer vaccine was provided on day 141 and subsequent doses were provided on days 148, 155, 162, and 192. FIG. 13 shows that the combined hormone blockade and vaccination treatment caused a reduction in PSA levels in this patient from a high of 50.3 on day 43 to a low of 1.12 on day 180, the last day on which a measurement was recorded.

Example 9

The autologous cancer vaccine described herein has been demonstrated to be safe in an initial Phase I trial with local advanced prostate cancer patients. This trial has been extended into Phase IIb. The primary endpoint of the Phase IIb study was clinical response (PSA levels and survival) in local advanced (T2 and T3) prostate cancer patients, with safety and immunologic responses as secondary endpoints.

Methods:

Tumour cells from 107 prostatectomy patients were collected (HCPA—Porto Alegre—Brazil). Sixty-three (59%) patients with T4, T3 or T2 prostate cancer with co-morbidity factors were enrolled. Twenty-three patients received the vaccine and 40 were in the control group. The vaccinated group was composed of patients having more advanced tumours, with 83% of the patients in the vaccinated group having either T3 or T4 prostate cancer, as compared to 35% of the control group. In the vaccinated group, 22% of patients were N+ (spread to local lymph nodes) and in the control group 2.5% of patients were N+. The PSA pre-surgery average was 16.15 ng/ml in the vaccinated group and 15.74 ng/ml in the control group. Average Gleason scores were 7.5 (vaccinated) and 6.9 (not vaccinated) and the age was similar 64 (not vaccinated) and 63 (vaccinated).

The autologous cancer vaccine was prepared as per Example 7 and was given by intradermal injections, once per week for 4 weeks, then once per month for 2 months, then once after three months. The first two doses of the autologous cancer vaccine also contained BGC as an adjuvant. DTH was measured 48 hours after the vaccine doses that did not contain BCG. PBMCs were collected via apheresis at baseline and D54 for T cell proliferation assays in some patients. Clinical follow-up was performed and all standard care was given to all patients.

Figure 14:
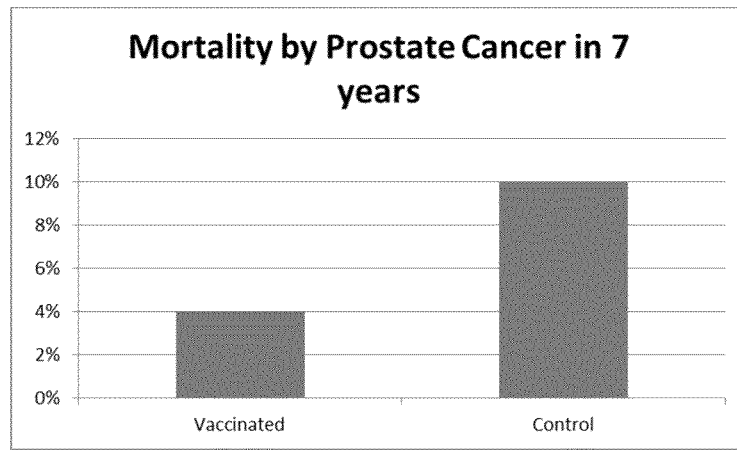
FIG. 14 shows clinical results from Phase I/II clinical trials in patients treated with the autologous cancer cell vaccine or control.
Figure 14:
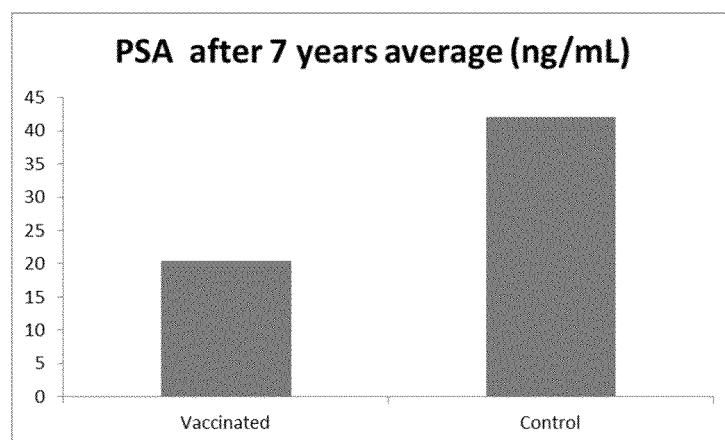
Figure 14:
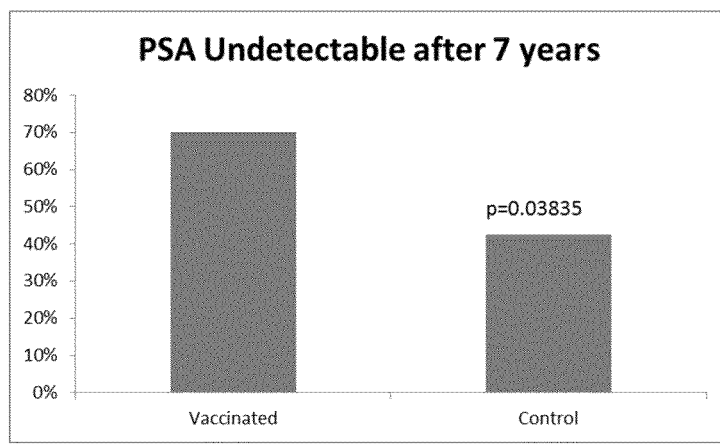

Results:

The overall average follow up was 7 years. No grade 3 or 4 toxicity attributable to the vaccine was noted. Side effects were largely limited to grade 1 or 2 injection site reactions. DTH was positive (equal to or higher than 5 mm) in 73% of the vaccinated patients. Cancer-related mortality was 4% (1/23) in the vaccinated group and 10% (4/40) in the non-vaccinated group (FIG. 14A). The average PSA level after 7 years was 20.4 ng/ml in the vaccinated group and 42 ng/ml in the non-vaccinated group (FIG. 14B). PSA was undetectable (less than 0.04 ng/ml) in 70% (16/23) of the vaccinated patients and in 42.5% (17/40) of the non-vaccinated patients after 5 years of follow up (p=0.03853) (FIG. 14C). In vitro specific T cell proliferation was demonstrated in vaccinated patients.

CONCLUSIONS

The autologous cancer vaccine described herein is a safe and well-tolerated vaccine. There is evidence of clinical activity and immune changes in selected patients.

The above disclosure generally describes the present invention. Although specific terms have been employed herein, such terms are intended in a descriptive sense and not for purposes of limitation.

All publications, patents and patent applications are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

What is claimed is:

1. A method for making isolated immunogenic cancer cells or an immunogenic extract thereof comprising both MHCI and MHCII, the method comprising:
   isolating cancer cells from a subject during a biopsy procedure or during surgical removal of a tumour;
   inducing expression of MHCII on the cancer cells isolated from a subject;
   incubating the cancer cells with a non-self antigen so that the non-self antigen will be bound to expressed MHCII;
   killing the cancer cells; and
   identifying MHCII-positive cancer cells after MHCII induction.

2. The method of claim 1, wherein the identifying MHCII-positive cells after MHCII induction is after incubating the cancer cells with a non-self antigen and before killing the cancer cells.

3. The method of claim 2, further comprising separating the MHCII-positive cancer cells from MHCII-negative cancer cells to obtain a purified composition containing the MHCII-positive cells.

4. The method of claim 1, further comprising cryo-preserving the killed cancer cells.

5. The method of claim 1, wherein the cells are killed by lethal irradiation, freezing and thawing in the absence of a cryo-preservation agent, or treatment with a cytotoxic compound.

6. The method of claim 1, wherein the MHCII is induced on the cancer cells using an MHCII-inducing agent.

7. The method of claim 6, wherein the MHCII-inducing agent is a cytokine, an MHCII expression construct or an MHCII-expressing cell that will fuse with the cancer cells.

8. The method of claim 7, wherein the cytokine is IFN-α, IFN-β, IFN-γ, IL-4, IL-13, IL-23, TNF-α, or a combination thereof.

9. The method of claim 1, wherein the non-self antigen is a non-human antigen.

10. The method of claim 9, wherein said non-self antigen is selected from thyroglobulin, β-galactosidase, dextran, polylysine, tuberculin derived protein, ovalbumin (OVA), serum albumin, and keyhole limpet hemocyanin (KLH), and a combination thereof.

11. The method of claim 1, wherein said non-self antigen is not a bovine antigen.

12. The method of claim 11, wherein said non-self antigen is not BSA.

13. The method of claim 1, wherein said inducing step is in a medium free of BSA.

14. The method of claim 10, wherein said non-self antigen is bovine serum albumin.

15. The method of claim 8, wherein the cytokine is IFN-γ.

16. The method of claim 1, wherein the cancer cells are derived from a solid tumor.

17. The method of claim 16, wherein the cancer cells are derived from a solid tumor selected from the group consisting of breast cancer, colorectal cancer, melanoma, ovarian cancer, pancreatic cancer, gastric cancer, and prostate cancer.

18. The method of claim 17, wherein the cancer cells are derived from a prostate cancer.

19. An autologous cancer vaccine comprising isolated immunogenic cancer cells or an immunogenic extract thereof together with at least one adjuvant, wherein the immunogenic cancer cells express both MHCI and MHCII on their cell surface or the immunogenic extract thereof comprises both MHCI and MHCII, wherein a cancer antigen is bound to said MHCI and a non-self antigen is bound to said MHCII.

20. The vaccine of claim 19, wherein the adjuvant is selected from monophosphoryl Lipid A/synthetic trehalose dicorynomycolate (MPL-TDM), AS021/AS02, nonionic block co-polymer adjuvants, aluminum phosphate, R-848, imiquimod, PAM3CYS, poly (I:C), loxoribine, bacille Calmette-Guerin (BCG), Corynebacterium parvum, CpG oligodeoxynucleotides (ODN), cholera toxin derived antigens, CTA 1-DD, lipopolysaccharide adjuvants, complete Freund's adjuvant, incomplete Freund's adjuvant, saponin, mineral gels, aluminum hydroxide, lysolecithin, pluronic polyols, oil or hydrocarbon emulsions in water, keyhole limpet hemocyanins (KLH), and combinations thereof.

21. The vaccine of claim 20, comprising from about 5% to about 100% MHCII-positive cancer cells, based on the total number of cells in the vaccine.

22. The vaccine of claim 21, comprising at least about 50%, 90%, or 99% MHCII-positive cancer cells.

23. The vaccine of claim 20, provided in divided doses for multiple inoculations.

24. The vaccine of claim 23, provided in seven divided doses, wherein each dose comprises from about $1 \times 10^4$ to about $1 \times 10^9$ cancer cells.

25. The vaccine of claim 24, wherein each dose comprises about $1 \times 10^7$ cancer cells.

26. The vaccine of claim 19, wherein the non-self antigen is a non-human antigen.

27. The vaccine of claim 26, wherein said non-self antigen is selected from thyroglobulin, β-galactosidase, dextran, polylysine, tuberculin derived protein, ovalbumin (OVA), serum albumin, and keyhole limpet hemocyanin (KLH), and a combination thereof.

28. The vaccine of claim 19, wherein said non-self antigen is not a bovine antigen.

29. The vaccine of claim 28, wherein said non-self antigen is not BSA.

30. The vaccine of claim 19, further comprising at least one excipient, carrier, buffer, stabilizer, or a combination thereof.

31. The vaccine of claim 19, wherein the cancer cells are derived from a solid tumor.

32. The vaccine of claim 31, wherein the cancer cells are derived from a solid tumor selected from the group consisting of breast cancer, colorectal cancer, melanoma, ovarian cancer, pancreatic cancer, gastric cancer, and prostate cancer.

33. The vaccine of claim 32, wherein the cancer cells are derived from a prostate cancer.

34. Isolated immunogenic cancer cells that express both MHCI and MHCII on their cell surface or an immunogenic extract thereof comprising both MHCI and MHCII, wherein a cancer antigen is bound to said MHCI and a non-self antigen is bound to said MHCII, wherein said non-self antigen is selected from thyroglobulin, β-galactosidase, dextran, polylysine, tuberculin derived protein, ovalbumin (OVA), bovine serum albumin (BSA), sheep serum albumin, goat serum albumins, or fish serum albumin, and keyhole limpet hemocyanin (KLH), and a combination thereof.

35. The cells of claim 34, wherein the non-self antigen is not BSA.

36. The cells of claim 34, wherein said non-self antigen is bovine serum albumin.

37. The cells of claim 34, wherein the cancer cells are derived from a solid tumor.

38. The cells of claim 37, wherein the cancer cells are derived from a solid tumor selected from the group consisting of breast cancer, colorectal cancer, melanoma, ovarian cancer, pancreatic cancer, gastric cancer, and prostate cancer.

39. The cells of claim 38, wherein the cancer cells are derived from a prostate cancer.

40. A method for treating cancer in a subject, the method comprising administering isolated immunogenic cancer cells, or an immunogenic extract thereof comprising both MHCI and MHCII, to the subject, wherein the cells are autologous to the subject and express both MHCI and MHCII on their cell surface, and wherein a cancer antigen is bound to said MHCI and a non-self antigen is bound to said MHCII.

41. The method of claim 40, wherein the non-self antigen is a non-human antigen.

42. The method of claim 41, wherein said non-self antigen is selected from thyroglobulin, β-galactosidase, dextran, polylysine, tuberculin derived protein, ovalbumin (OVA), serum albumin, and keyhole limpet hemocyanin (KLH), and a combination thereof.

43. The method of claim 40, wherein said non-self antigen is not a bovine antigen.

44. The method of claim 43, wherein said non-self antigen is not BSA.

45. The method of claim 40, wherein the cells are administered concurrently or sequentially with at least one of conventional chemotherapy, radiotherapy, hormone therapy, and biotherapy.

46. The method of claim 45, wherein the cells are administered before or after surgical tumour resection.

47. The method of claim 40, wherein the cells are administered as an ongoing maintenance therapy.

48. The method of claim 47, wherein the cells are administered weekly, monthly, every 3 months, every 6 months, yearly, or a combination thereof.

49. The method of claim 40, wherein the cells are administered when a sign of cancer relapse is observed.

50. The method of claim 40, wherein said non-self antigen is bovine serum albumin.

51. The method of claim 40, wherein the cancer cells are derived from a solid tumor.

52. The method of claim 51, wherein the cancer cells are derived from a solid tumor selected from the group consisting of breast cancer, colorectal cancer, melanoma, ovarian cancer, pancreatic cancer, gastric cancer, and prostate cancer.

53. The method of claim 52, wherein the cancer cells are derived from a prostate cancer.

54. A method for making isolated immunogenic cancer cells or an immunogenic extract thereof comprising both MHCI and MHCII, the method comprising:
    inducing expression of MHCII on cancer cells isolated from a subject;
    incubating the cancer cells with a non-self antigen so that the non-self antigen will be bound to expressed MHCII, wherein the non-self antigen is selected from thyroglobulin, β-galactosidase, dextran, polylysine, tuberculin derived protein, ovalbumin (OVA), serum albumin, and keyhole limpet hemocyanin (KLH), and a combination thereof;
    killing the cancer cells; and
    identifying MHCII-positive cancer cells after MHCII induction.

55. A method for making isolated immunogenic cancer cells or an immunogenic extract thereof comprising both MHCI and MHCII, the method comprising:
    inducing expression of MHCII in a medium free of BSA on cancer cells isolated from a subject;
    incubating the cancer cells with a non-self antigen so that the non-self antigen will be bound to expressed MHCII;
    killing the cancer cells; and
    identifying MHCII-positive cancer cells after MHCII induction.

56. A method for making isolated immunogenic cancer cells or an immunogenic extract thereof comprising both MHCI and MHCII, the method comprising:
    inducing expression of MHCII on cancer cells isolated from a subject, wherein the cancer cells are derived from a prostate cancer;
    incubating the cancer cells with a non-self antigen so that the non-self antigen will be bound to expressed MHCII;
    killing the cancer cells; and
    identifying MHCII-positive cancer cells after MHCII induction.

* * * * *